(12) United States Patent
Brissette et al.

(10) Patent No.: US 7,687,265 B2
(45) Date of Patent: Mar. 30, 2010

(54) FOXN1 AND PIGMENTATION

(75) Inventors: Janice Brissette, Charlestown, MA (US); Lorin Weiner, Charlestown, MA (US); Rong Han, Malden, MA (US); Rebecca Campen, Savannah, GA (US)

(73) Assignee: The General Hospital Corporation, Boston, MA (US)

( * ) Notice: Subject to any disclaimer, the term of this patent is extended or adjusted under 35 U.S.C. 154(b) by 355 days.

(21) Appl. No.: 10/997,202

(22) Filed: Nov. 24, 2004

(65) Prior Publication Data

US 2005/0191242 A1 Sep. 1, 2005

Related U.S. Application Data

(60) Provisional application No. 60/525,093, filed on Nov. 25, 2003.

(51) Int. Cl.
*C12N 5/00* (2006.01)
*G01N 33/53* (2006.01)

(52) U.S. Cl. ......................................... 435/375; 435/7.2

(58) Field of Classification Search .................... 800/3; 435/455, 375, 7.2
See application file for complete search history.

(56) References Cited

U.S. PATENT DOCUMENTS

| | | |
|---|---|---|
| 2002/0064876 A1 | 5/2002 | Yoon |
| 2002/0177218 A1 | 11/2002 | Fang et al. |
| 2002/0192738 A1 | 12/2002 | Brissette et al. |
| 2003/0095937 A1 | 5/2003 | Koeffler et al. |
| 2003/0121062 A1 | 6/2003 | Radcliffe et al. |
| 2004/0040052 A1 | 2/2004 | Radcliffe et al. |
| 2004/0096971 A1 | 5/2004 | Blackburn et al. |
| 2005/0022258 A1 | 1/2005 | Cui et al. |
| 2005/0260213 A1 | 11/2005 | Koenig et al. |
| 2006/0068494 A1 | 3/2006 | Perreault |
| 2006/0105977 A1 | 5/2006 | Christiano |
| 2006/0110469 A1 | 5/2006 | Luo et al. |
| 2006/0147429 A1 | 7/2006 | Diamond |
| 2006/0148080 A1 | 7/2006 | Diamond |
| 2006/0172304 A1 | 8/2006 | Fuchs et al. |
| 2006/0189546 A1 | 8/2006 | Ajami et al. |

FOREIGN PATENT DOCUMENTS

WO   WO 01/44461 A1   6/2001
WO   WO 01/85964 A2   11/2001

OTHER PUBLICATIONS

Yoon et al, Pigment Cell Research, 16: 159-163, 2003.*
Balciunaite et al, Nat Immunol, 3(11): 1102-1108, 2002.*
Vilador et al, (Analytical Biochemistry, 270: 207-219, 1999.*
Bader et al., "Transgenic Rats: Tools to Study the Function of the Renin-Angiotensin System," *Clin Exp. Pharmacol. Physiol.*, Suppl. 3:S81-S87 (1996).
Balciunaite et al., "Wnt glycoproteins regulate the expression of FoxN1, the gene defective in nude mice," *Nat. Immunol.*, 3(11):1102-1108 (2002).
Bouwstra et al., "Skin structure and mode of action of vesicles," *Adv. Drug Deliv. Rev.*, Suppl. 1:S41-S55 (2002).
Brissette et al., "The product of the mouse *nude* locus, *Whn*, regulates the balance between epithelial cell growth and differentiation," *Genes & Development*, 10:2212-2221(1996).
Cunliffe et al., "Complete rescue of the nude mutant phenotype by a wild-type *Foxn1* transgene," *Mamm. Genome*, 13(5):245-252 (2002).
DiSepio et al., "Characterization of loricrin regulation in vitro and in transgenic mice," *Differentiation*, 64(4):225-235 (1999).
Guo et al., "Targeting expression of keratinocyte growth factor to keratinocytes elicits striking changes in epithelial differentiation in transgenic mice," *EMBO J.*, 12(3):973-986 (1993).
Han et al., "Redefining the Skin's Pigmentary System with a Novel Tyrosinase Assay," *Pigment Cell Res.*, 15(4):290-297 (2002).
Hedley et al., "Fibroblasts Play a Regulatory Role in the Control of Pigmentation in Reconstructed Human Skin from Skin Types I and II," *Pigment Cell Res.*, 15(1):49-56 (2002).
Jang et al., "Loricrin Expression in Cultured Human Keratinocytes Is Controlled by a Complex Interplay between Transcription Factors of the Sp1, CREB, AP1, and AP2 Families," *J. Biol. Chem.*, 277(44):42268-42279 (2002).
Kunisada et al., "Transgene expression of steel factor in the basal layer of epidermis promotes survival, proliferation, differentiation and migration of melanocyte precursors," *Development*, 125(15):2915-2923 (1998).
Lee et al., "Association between Mouse *nude* Gene Expression and the Initiation of Epithelial Terminal Differentiation," *Dev. Biol.*, 208(2):362-374 (1999).
Lei et al., "A Melanocyte-Keratinocyte Coculture Model to Assess Regulators of Pigmentation in Vitro," *Anal. Biochem.*, 305(2):260-268 (2002).

(Continued)

*Primary Examiner*—Anne-Marie Falk
*Assistant Examiner*—Magdalene K Sgagias
(74) *Attorney, Agent, or Firm*—Fish & Richardson P.C.

(57) ABSTRACT

The present invention provides methods and compositions for modulating skin pigmentation.

10 Claims, 1 Drawing Sheet

OTHER PUBLICATIONS

Nehls et al., "Two Genetically Separable Steps in the Differentiation of Thymic Epithelium," *Science*, 272:886-889 (1996).

Santiago et al., "Ephrin-B ligands play a dual role in the control of neural crest cell migration," *Development*, 129(15):3621-3632 (2002).

Schorpp et al., "Characterization of mouse and human nude genes," *Immunogenetics*, 46(6):509-515 (1997).

Sinha et al., "Defining the Regulatory Factors Required for Epidermal Gene Expression," *Mol. Cell. Biol.*, 20(7):2543-2555 (2000).

Virador et al., "A Standardized Protocol for Assessing Regulators of Pigmentation," *Anal. Biochem.*, 270(2):207-219 (1999).

Weiner et al., "FoxN1 and the Acquisition of Pigmentation," *Pigment Cell Res.*, Abstract No. 46, 16(4):425 (2003).

Yarosh et al., "Effect of topically applied T4 endonuclease V in liposomes on skin cancer in xeroderma pigmentosum: a randomized study," *Lancet*, 357:926-929 (2001).

Yoon et al., "Co-Culture of Mouse Epidermal Cells for Studies of Pigmentation," *Pigment Cell Res.*, 16(2):159-163 (2003).

Alge et al., "PUVA downregulates *whn* expression in primary mouse keratinocytes," J. Photochem. Photobiol. B, 64:75-81 (2001).

Baxter and Brissette, "Role of the *nude* gene in epithelial terminal differentiation," J. Invest. Dermatol., 118:303-309 (2002).

Frank et al., "Exposing the human *nude* phenotype," Nature, 398:473-474 (1999).

Li et al., "Foxn1 promotes keratinocyte differentiation by regulating the activity of protein kinase C," Differentiation, 75:694-701 (2007).

Prowse et al., "Ectopic expression of the *nude* gene induces hyperproliferation and defects in differentiation: implications for the self-renewal of cutaneous epithelia," Dev. Biol., 212:54-67 (1999).

Weiner et al., "Dedicated epithelial recipient cells determine pigmentation patterns," Cell, 130:932-942 (2007).

\* cited by examiner

FOXN1 AND PIGMENTATION

CROSS-REFERENCE TO RELATED APPLICATION

This application claims priority to U.S. Ser. No. 60/525,093, filed Nov. 25, 2003, the contents of which are hereby incorporated by reference.

FEDERALLY SPONSORED RESEARCH OR DEVELOPMENT

The invention described herein was supported in part by Grant No. RO1-AR45284 from the National Institutes of Health. The United States Government retains certain rights in this invention.

BACKGROUND OF THE INVENTION

Skin pigmentation plays an important role in protecting the body from the harmful effects of ultraviolet rays. Pigmentation involves interactions between epithelial cells, such as keratinocytes, and melanocytes. Melanocytes synthesize melanin in specialized cytoplasmic organelles (melanosomes) and, via dendritic processes, transfer pigment to multiple keratinocytes. Melanin gives the skin its color and photoprotective properties. Degradation or storage of the melanin in the keratinocytes influences the intensity of pigmentation. Nonuniform distribution of melanin causes skin pathologies such as vitiligo, chloasma and ephelis.

SUMMARY OF THE INVENTION

The invention is based, inter alia, on the inventors' discovery that the Foxn1 signal transduction pathway is important for the maintenance and/or appearance of skin. In particular, the inventors have found that the Foxn1 signal transduction pathway modulates skin color, e.g., pigmentation. Therefore, the inventors have identified the Foxn1 signal transduction pathway as a target for screening, diagnostic and treatment methods for the modulation of skin color, e.g., pigmentation.

Accordingly, in one respect, the invention features a method for identifying an agent that modulates skin color, e.g., pigmentation. The method includes identifying an agent that modulates, e.g., increases or decreases (e.g., permanently or temporarily), the expression, activity or levels of a component of the Foxn1 signal transduction pathway, e.g., Foxn1; and correlating the ability of an agent to modulate Foxn1 expression, levels or activity with the ability to modulate skin color. The method can further include selecting an identified agent, e.g., an agent that modulates skin color, e.g., modulates skin pigmentation.

In one embodiment, the agent is identified by evaluating the ability of a test agent to interact with, e.g., to bind, Foxn1. In another embodiment, the agent is identified by evaluating the effect of a test agent to interact with a Foxn1 regulatory region, e.g., a promoter. In another embodiment, the agent is identified by evaluating the effect of a test agent on a melanocyte cell culture or co-culture, e.g., a culture comprising a melanocyte and a non-melanocyte. In another embodiment, the agent is identified by evaluating, e.g., quantitatively or qualitatively evaluating, the ability of a test agent to modulate the skin color of a Foxn1 transgenic animal, e.g., a Foxn1 transgenic animal described herein.

The test agent can be, e.g., a nucleic acid (e.g., an antisense, siRNA, ribozyme), a polypeptide (e.g., an antibody or antigen-binding fragment thereof), a peptide fragment, a peptidomimetic, or a small molecule (e.g., a small organic molecule with a molecular weight of less than 2000 daltons). In another preferred embodiment, the test agent is a member of a combinatorial library, e.g., a peptide or organic combinatorial library, or a natural product library. In a preferred embodiment, a plurality of test agents, e.g., library members, is tested. Preferably, the test agents of the plurality, e.g., library, share structural or functional characteristics. The test agent can also be a crude or semi-purified extract, e.g., a botanical extract such as a plant extract, or algal extract.

The method can include correlating the effect of the agent on the Foxn1 signal transduction pathway with a predicted effect of the agent on a mammal, e.g., a human, e.g., by providing (e.g., to the government, a health care provider, insurance company or patient) informational, marketing or instructional material, e.g., print material or computer readable material (e.g., a label, an email), related to the agent or its use, identifying the effect of the agent as a possible or predicted effect of the agent in a mammal, e.g., a human. The method can include identifying the agent as a pigmentation-modulating agent, e.g., in humans, if it increases Foxn1 expression, levels or activity, compared to a reference. The identification can be in the form of informational, marketing or instructional material, e.g., as described herein. In one embodiment, the method includes correlating a value for the evaluated parameter with altered pigmentation or probability of altered pigmentation, e.g., generating a dataset correlating a value for the evaluated parameter with altered pigmentation or probability of altered pigmentation.

In one embodiment, the method includes two evaluating steps, e.g., the method includes a first step of evaluating the test agent in a first system, e.g., a cell-free, cell-based, tissue system or animal model, and a second step of evaluating the test agent in a second system, e.g., a second cell or tissue system or in a non-human animal. In one embodiment, one of the evaluating steps includes evaluating the effect of the agent on a subject's skin or skin explant, e.g., evaluating the presence, extent or type of pigmentation of the skin. The subject can be an experimental animal or a human. In one embodiment, the first evaluation includes testing the effect of the test agent on a Foxn1 promoter which is linked to a heterologous sequence such as a reporter polypeptide, and the second evaluation includes administering the test agent to a system, e.g., a cell based or animal system and evaluating effect of the agent on skin color. In some embodiments, the method includes two evaluating steps in the same type of system, e.g., the agent is re-evaluated in a non-human animal after a first evaluation in the same or a different non-human animal. The two evaluations can be separated by any length of time, e.g., days, weeks, months or years.

In a preferred embodiment, the identifying step includes: (a) providing an agent to a cell, tissue or non-human animal whose genome includes an exogenous nucleic acid that includes a regulatory region of a component of the Foxn1 signal transduction pathway, e.g., a Foxn1 promoter, operably linked to heterologous sequence, e.g., a nucleotide sequence encoding a reporter polypeptide (e.g., a colorimeteric (e.g., LacZ) or flourescently detectable reporter polypeptide, e.g. GFP, EGFP, BFP, RFP); (b) evaluating the ability of a test agent to modulate the expression of the reporter polypeptide in the cell, tissue or non-human animal; and (c) selecting a test agent that modulates the expression of the reporter polypeptide as an agent that modulates a component of the Foxn1 signal transduction pathway (e.g., modulates Foxn1).

In one embodiment, the animal is an experimental animal. The animal can be wild-type or a transgenic experimental animal, e.g., a Foxn1 transgenic rodent, e.g., a Foxn1 transgenic mouse described herein. The subject may also be a human. In a preferred embodiment, the evaluating step comprises administering the agent to the subject and evaluating skin pigmentation. In another embodiment, the cell or tissue is a skin cell, e.g., an epithelial cell, such as a keratinocyte, e.g., a basal keratinocyte, a melanocyte, or tissue, e.g., a skin explant. In yet another embodiment, a cell, e.g., a skin cell, or a tissue, e.g., a skin explant, is of a transgenic animal.

In another aspect, the invention features a transgenic non-human animal having a Foxn1 transgene. Some embodiments feature a transgenic cell (e.g., a keratinocytes), tissue (e.g., skin) or non-human mammal (e.g., rodents, e.g., mice, rats, guinea pigs, rabbits) containing a Foxn1 transgene which is operably linked to a promoter sequence sufficient to direct Foxn1 expression in a cell type substantially lacking endogenous Foxn1 protein, e.g., epithelial cells, keratinocytes, basal keratinocytes, e.g., of the epidermis or hair follicles. Examples of such promoters include Krt5, Keratin 14 or loricrin promoters. Such a cell, tissue, or animal can have altered skin appearance, e.g., altered pigmentation. The Foxn1 transgene may be contained in the germ and/or somatic cells; alternatively, the Foxn1 transgene may be contained only in a certain type of cell, such as epithelial cells, e.g., basal epithelial cells of the epidermis or hair follicles.

Another aspect of the invention features an isolated nucleic acid sequence encoding a Foxn1 polypeptide, or a functional fragment or variant thereof, operably linked to an expression control sequence, e.g., a sequence that results in cell-type specific gene expression, e.g,. expression in epithelial cells, keratinocytes, melanocytes, hair follicles, or other skin cells. In one embodiment, the expression control sequence includes sequences from Krt5, e.g., a transcription factor binding site (e.g., a cell-type specific transcription factor binding site), a regulatory sequence, a promoter, an element thereof, an enhancer or an element thereof. Typically the expression control sequence is sufficient to drive expression of Foxn1 in a cell type substantially lacking endogenous Foxn1 protein, such as epithelial cells (preferably basal epithelial cells) of the epidermis or hair follicles. In another embodiment, the expression control sequence includes an inducible sequence, e.g., a steroid-regulated control sequence or metallothionin control sequence. In one embodiment, the control sequence includes a functional fragment of the CMV promoter or the entire CMV promoter. In one embodiment, the control sequence includes a constitutively active promoter or a functional fragment thereof. The nucleic acid sequence can also include 3' untranslated region, e.g., the 3' untranslated region of Krt14 or a polyadenylation sequence. The nucleic acid sequence can also include a Kozak sequence. The nucleic acid can further include an intron, e.g., an intron that facilitates translation, e.g., an intron from the β-globin gene (e.g., from rabbit or another species).

The nucleic acid may be an integral part of a linear construct or of a vector, e.g., a plasmid, e.g., an expression plasmid or a replicating plasmid, or a viral vector, e.g. lambda-ZAP. The vector may be harbored in a host, e.g., *E. coli* or bacteriophage. Also included are host cells (e.g., mammalian host cells) that include the nucleic acid and/or vectors described herein. The invention also features viruses capable of introducing nucleic acids into mammalian cells (e.g., epithelial cells), the viruses including a nucleic acid described herein, e.g., a nucleic acid that can express Foxn1 or a functional fragment thereof. The virus can be an adenovirus or an adeno-associated virus.

In another aspect, the invention features a method of treating a subject. The method includes (a) identifying a subject desirous, or in need, of altered skin pigmentation; and (b) administering to the subject an agent that modulates a component of the Foxn1 signal transduction pathway in the subject, e.g., administering to the subject an effective amount of an agent that increases or decreases the activity, level or expression of a component of the Foxn1 signal transduction pathway, e.g., an agent described herein. In one embodiment, the agent is a Foxn1 polypeptide. In another embodiment, the agent is fibroblast growth factor 2, α-melanocyte stimulating hormone, α-melanocyte stimulating hormone, β-melanocyte stimulating hormone, endothelin 1, endothelin 3, transforming growth factor β1 and nerve growth factor. Preferably, the agent is administered to the subject's skin, e.g., topically.

In a preferred embodiment, the agent is administered via a liposome carrier, e.g., a lecithin liposome or a alkylphospholipid liposome. The agent can be administered to the face, chest, neck, hands, and other regions of the body. The treatment can involve more than one administration, e.g., at least two, three, or four administrations, of the agent. The treatment can also involve daily administration of the agent. In a preferred embodiment, the agent is a Foxn1 polypeptide, a fragment thereof, or a nucleic acid that encodes such polypeptides. The nucleic acid can be delivered by a variety of means including viral, e.g., an adeno-viral or AAV gene delivery system. In a preferred embodiment, the method includes evaluating the effect of the administration on skin pigmentation.

In one embodiment, the method includes administering the agent in combination with a second treatment, e.g., a second treatment for a pigmentation-related disorder such as vitiligo, albinism or melanoma.

In some embodiments, the method includes evaluating the subject for one or more of: skin color, skin cancer, UV sensitivity. The evaluation can be performed before, during, and/or after the administration of the agent. For example, the evaluation can be performed at least 1 day, 2 days, 4, 7, 14, 21, 30 or more days before and/or after the administration.

In a preferred embodiment, the administration of an agent can be initiated: when the subject begins to show signs of a pigmentation-related disorder; when a pigmentation-related disorder (e.g., melanoma) is diagnosed; at the time a treatment for a pigmentation-related disorder is begun or begins to exert its effects; or generally, as is needed to maintain skin health.

The period over which the agent is administered (or the period over which clinically effective levels are maintained in the subject) can be long term, e.g., for six months or more or a year or more, or short term, e.g., for less than a year, six months, one month, two weeks or less.

The identification of a subject in need of altered pigmentation can be performed e.g., by the subject, by a health care provider, by a provider of cosmetics or another party. The agent may be administered, e.g., by the subject, by a health care provider, by a provider of cosmetics or another party. Likewise, the evaluation of the effect on skin pigmentation may be performed, e.g., by the subject, by a health care provider, by a provider of cosmetics or another party. Suitable subjects include subjects who have or are at risk for: melanoma, albinism, and/or vitiligo.

An agent that increases Foxn1 signaling to thereby increase pigmentation can be, for example: (a) a polypeptide component of the Foxn1 signal transduction pathway, e.g., a Foxn1 polypeptide, or a functional fragment or variant thereof; (b) a peptide or protein agonist or antagonist of a component of the Foxn1 signal transduction pathway that modulates an activity of the Foxn1 signal transduction pathway, e.g., modulates Foxn1; (c) a small molecule that modulates expression of a component of the Foxn1 signal transduction pathway, e.g., Foxn1, e.g., by binding to the promoter region of its gene; (d) a chemical compound, e.g., an organic compound, e.g., a naturally occurring or synthetic organic compound that modulates expression of a component of the Foxn1 signal transduction pathway, e.g., Foxn1; (e) a nucleotide sequence encoding a Foxn1 signal transduction pathway polypeptide, or a fragment or analog thereof; or (f) an antibody, e.g., an antibody that binds to and stabilizes or assists the binding of a Foxn1 pathway component to a binding partner. The nucleotide sequence can be a genomic sequence or a cDNA sequence. The nucleotide sequence can include: a Foxn1 pathway component coding region; a promoter sequence, e.g., a promoter sequence from a Foxn1 pathway component gene or from another gene; an enhancer sequence; untranslated regulatory sequences, e.g., a 5' untranslated region (UTR), e.g., a 5' UTR from a Foxn1 gene or from another gene, a 3' UTR, e.g., a 3' UTR from a Foxn1 gene or from another gene; a polyadenylation site; an insulator sequence. In another preferred embodiment, the level of a component of the Foxn1 signal transduction pathway, e.g., Foxn1, is increased by increasing the level of expression of an endogenous component of the Foxn1 signal transduction pathway, e.g., Foxn1, e.g., by increasing transcription of the Foxn1 gene or increasing Foxn1 mRNA stability. In a preferred embodiment, transcription of the Foxn1 gene is increased by: altering the regulatory sequence of the endogenous Foxn1 gene, e.g., in a somatic cell, e.g., by the addition of a positive regulatory element (such as an enhancer or a DNA-binding site for a transcriptional activator); the deletion of a negative regulatory element (such as a DNA-binding site for a transcriptional repressor) and/or replacement of the endogenous regulatory sequence, or elements therein, with that of another gene, thereby allowing the coding region of the Foxn1 gene to be transcribed more efficiently.

An agent that decreases Foxn1 signaling to thereby decrease pigmentation can be, for example: a Foxn1 binding protein, e.g., a soluble Foxn1 binding protein that binds and inhibits a Foxn1 activity, or inhibits the ability of a Foxn1 to interact with a binding partner; an antibody that specifically binds to the Foxn1 protein, e.g., an antibody that disrupts Foxn1's ability to bind to a binding partner; a mutated inactive Foxn1 or fragment thereof which binds to Foxn1 but disrupts a Foxn1 activity; a Foxn1 nucleic acid molecule that can bind to a cellular Foxn1 nucleic acid sequence, e.g., mRNA, and can inhibit expression of the protein, e.g., an antisense, siRNA molecule or Foxn1 ribozyme; an agent which decreases Foxn1 gene expression, e.g., a small molecule which binds the promoter of Foxn1. In another preferred embodiment, Foxn1 is inhibited by decreasing the level of expression of an endogenous Foxn1 gene, e.g., by decreasing transcription of the Foxn1 gene. In a preferred embodiment, transcription of the Foxn1 gene can be decreased by: altering the regulatory sequences of the endogenous Foxn1 gene, e.g., by the addition of a negative regulatory sequence (such as a DNA-binding site for a transcriptional repressor), or by the removal of a positive regulatory sequence (such as an enhancer or a DNA-binding site for a transcriptional activator). In another preferred embodiment, the antibody which binds the Foxn1 is a monoclonal antibody, e.g., a humanized chimeric or human monoclonal antibody.

In another aspect, the invention also features compositions containing an agent, e.g., an agent described herein, e.g., an agent identifying by a screening method described herein, that modulates the expression, activity, or level of a component of the Foxn1 signal transduction pathway, e.g., Foxn1, for modulating skin color, e.g., skin pigmentation. In a preferred embodiment, the composition is a cosmetic composition, e.g., formulated for topical administration. The composition is effective to modulate skin pigmentation when applied to the skin, e.g., for a period of at least 1 day, more preferably at least 7 days, even more preferably 14, 10 30, 60, 90 days, or it can be effective to modulate skin pigmentation for a longer term, e.g., at least 6 to 9 months or longer. In a preferred embodiment, the composition also has a fragrance, a preservative, or other cosmetic ingredient, e.g., a moisturizer, or sunscreen agent, e.g., octyl methoxycinnamate, aminobenzoic acid, oxybenzone, padimate O, homosalate, or titanium dioxide. The composition can be provided in an oil, cream, lotion, soap, shampoo, foam, gel, or other cosmetic preparation. In a preferred embodiment, the composition also has a cosmetic ingredient, e.g., a fragrance or moisterizer.

In another aspect, the invention features a method of modulating skin pigmentation in a subject. The method includes supplying to the subject a composition containing an agent that affects the expression, activity or level of a component of the Foxn1 signal transduction pathway, e.g., Foxn1, e.g., an agent described herein, e.g., an agent identified by a screening method described herein, preferably with application instructions.

In another aspect, the invention features a kit for modulating skin pigmentation of a subject which includes a composition described herein, e.g., a composition containing an agent that affects the expression, activity, or level of a component of the Foxn1 signal transduction pathway, e.g., Foxn1; and instructions for use, e.g., application instructions. In a preferred embodiment, the composition also has a cosmetic ingredient, e.g., a fragrance or moisturizer.

An effective amount of the agent of the present invention is defined as the amount of a composition which, upon administration to a subject, modulates pigmentation in the subject. The effective amount to be administered to a subject is typically based on a variety of factors including age, sex, surface area, weight, and conditions of the skin. Body surface area may be approximately determined from height and weight of the patient. See, e.g., Scientific Tables, Geigy Pharmaceuticals, Ardley, N.Y., 1970, 537. Effective doses will vary, as recognized by those skilled in the art, dependent on route of administration, excipient usage, and the possibility of co-usage with other treatments such as usage of other pigmentation-modulating compounds.

In another aspect, the invention provides a method of determining if a subject is at risk for or has a pigmentation-related disorder, e.g., vitiligo, hyperpigmentation or melanoma. The method includes: (a) evaluating the level, activity, expression and/or genotype of a Foxn1 molecule in a subject, e.g., in a biological sample of the subject, and (b) correlating an alteration in a Foxn1 molecule, e.g., a non-wild-type level, activity, expression, and/or genotype of Foxn1 with a risk for or presence of a pigmentation-related disorder, e.g., vitiligo. Correlating means identifying the alteration as a risk or diagnostic factor of vitiligo, e.g., providing a print material or computer readable medium, e.g., an informational, diagnostic, marketing or instructional print material or computer readable medium, e.g., to the subject or to a health care provider, identifying the alteration as a risk or diagnostic factor for vitiligo, hyperpigmentation or melanoma.

In a preferred embodiment, the method includes diagnosing a subject as being at risk for or having vitiligo. In another preferred embodiment, the method includes prescribing or beginning a treatment for vitiligo in the subject. In some embodiments, the method includes performing a second diagnostic test for vitiligo, e.g., the evaluation of the level, activity, expression and/or genotype of a Foxn1 molecule in a subject can be repeated, e.g., by performing the same or a different determination as described herein, or by performing another diagnostic test for vitiligo, hyperpigmentation or melanoma known in the art, e.g., evaluating tyrosinase activity in the subject (see, e.g., Han et al. (2002) *Pigment Cell Res.* 15:290).

The subject is preferably a human, e.g., a human with a family history of vitiligo. The biological sample can be a cell sample, tissue sample, or at least partially isolated molecules, e.g., nucleic acids, e.g., genomic DNA, cDNA, mRNA, and/or proteins derived from the subject. Such methods are useful, e.g., for diagnosis of vitiligo or vitiligo risk.

In a preferred embodiment, the method includes one or more of the following: 1) detecting, in a biological sample of the subject, the presence or absence of a mutation that affects the expression of Foxn1, or detecting the presence or absence of a mutation in a region which controls the expression of the gene, e.g., a mutation in the 5' control region, the presence of a mutation being indicative of risk; 2) detecting, in a biological sample of the subject, the presence or absence of a mutation that alters the structure of Foxn1, the presence of a mutation being indicative of risk; 3) detecting, in a biological sample of the subject, the misexpression of Foxn1, at the mRNA level, e.g., detecting a non-wild-type level of a Foxn1 mRNA, non-wild-type levels of Foxn1 mRNA being associated with risk. Detecting misexpression can include ascertaining the existence of at least one of: an alteration in the level of a mRNA transcript of Foxn1 compared to a reference, e.g., as compared to a baseline value or to levels in a subject not at risk for an pigmentation-related disorder; the presence of a non-wild-type splicing pattern of a mRNA transcript of the gene; or a non-wild-type level of Foxn1 protein e.g., as compared to a reference, e.g., compared to a baseline value, or to levels in a subject not at risk for a pigmentation-related disorder; 4) detecting, in a biological sample of the subject, the misexpression of Foxn1, at the protein level, e.g., detecting a non-wildtype level of a Foxn1 polypeptide, decreased or increased levels of Foxn1 protein (e.g., compared to a control) being indicative of a risk. For example, the method can include contacting a sample from the subject with an antibody to Foxn1 protein; and 5) detecting, in a biological sample of the subject, a polymorphism, e.g., a SNP, in Foxn1, which is associated with vitiligo. In preferred embodiments the method includes: ascertaining the existence of at least one of: an insertion or a deletion of one or more nucleotides from Foxn1; a point mutation, e.g., a substitution of one or more nucleotides of the gene; a gross chromosomal rearrangement of the gene, e.g., a translocation, inversion, duplication or deletion. In a preferred embodiment, a SNP or haplotype associated with vitiligo risk is detected.

In one embodiment, detecting a mutation or polymorphism can include: (i) providing a probe or primer, e.g., a labeled probe or primer, that includes a region of nucleotide sequence which hybridizes to a sense or antisense sequence from Foxn1, or naturally occurring mutants thereof, or to the 5' or 3' flanking sequences naturally associated with Foxn1; (ii) exposing the probe/primer to nucleic acid of the subject; and (iii) detecting, e.g., by hybridization, e.g., in situ hybridization to the nucleic acid; or amplification of the nucleic acid, the presence or absence of the mutation or polymorphism.

In another aspect, the invention features a computer readable record encoded with (a) a subject identifier, e.g., a patient identifier, (b) one or more results from an evaluation of the subject, e.g., a diagnostic evaluation described herein, e.g., the level of expression, level or activity of Foxn1 in the subject, and optionally (c) a value for or related to a disease state, e.g., a value correlated with disease status or risk with regard to pigmentation, e.g., vitiligo or melanoma. In one embodiment, the invention features a computer medium having a plurality of digitally encoded data records. Each data record includes a value representing the level of expression, level or activity of Foxn1 in a sample, and a descriptor of the sample. The descriptor of the sample can be an identifier of the sample, a subject from which the sample was derived (e.g., a patient), a diagnosis, or a treatment (e.g., a preferred treatment). In a preferred embodiment, the data record further includes values representing the level of expression, level or activity of genes other than Foxn1 (e.g., other genes associated with loss of pigmentation or other genes on an array). The data record can be structured as a table, e.g., a table that is part of a database such as a relational database (e.g., a SQL database of the Oracle or Sybase database environments). The invention also includes a method of communicating information about a subject, e.g., by transmitting information, e.g., transmitting a computer readable record described herein, e.g., over a computer network.

In another aspect, the invention features a method of providing information, e.g., for making a decision with regard to the treatment of a subject having, or at risk for, a disorder described herein. The method includes (a) evaluating the expression, level or activity of Foxn1; optionally (b) providing a value for the expression, level or activity of Foxn1; optionally (c) comparing the provided value with a reference value, e.g., a control or non-disease state reference or a disease state reference; and optionally (d) based, e.g., on the relationship of the provided value to the reference value, supplying information, e.g., information for making a decision on or related to the treatment of the subject. In a preferred embodiment, the provided value relates to an activity described herein, e.g., to Foxn1 activity described herein. In a preferred embodiment, the decision is whether to administer a preselected treatment. In a preferred embodiment, the decision is whether a party, e.g., an insurance company, HMO, or other entity, will pay for all or part of a preselected treatment.

Also featured is a method of evaluating a sample. The method includes providing a sample, e.g., from the subject, and determining a gene expression profile of the sample, wherein the profile includes a value representing the level of expression of Foxn1. The method can further include comparing the value or the profile (i.e., multiple values) to a reference value or reference profile. The gene expression profile of the sample can be obtained by methods known in the art (e.g., by providing a nucleic acid from the sample and contacting the nucleic acid to an array). The method can be used to diagnose loss of pigmentation function, e.g., decreased or nonoptimal pigmentation, e.g., albinism or vitiligo, in a subject wherein misexpression of Foxn1, e.g., an decrease in expression of Foxn1, is an indication that the subject has or is disposed to having loss of pigmentation function, e.g., albinism or vitiligo. The method can be used to monitor a treatment in a subject. For example, the gene expression profile can be determined for a sample from a subject undergoing treatment. The profile can be compared to a reference profile or to a profile obtained from the subject prior to treatment or prior to onset of the disorder (see, e.g., Golub et al. (1999) *Science* 286:531).

DETAILED DESCRIPTION OF THE INVENTION

Figure 1:
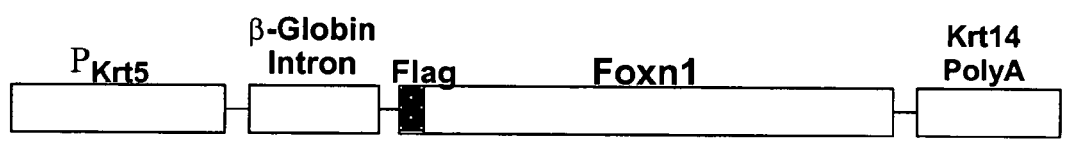
FIG. 1 is a diagram of the construct used to generate transgenic mice. The construct includes the murine Krt5 promoter, a rabbit beta-globin intron, a Flag epitope tag fused to the murine Foxn1 cDNA and a keratin 14 (Krt14) polyadenylation sequence (approximately 0.5 kb in size).

The inventors have identified the Foxn1 signal transduction pathway as a target for screening, diagnostic and treatment methods and related cosmetic and health compositions for modulating skin pigmentation.

Using the methods described herein, cosmetically desirable tanning of the skin can be achieved without exposure to damaging UV radiation. In addition, the methods described herein can also provide lighter or more consistent skin tones. Thus, the methods described herein provide a valuable cosmetic benefit. Significant health benefits can also be provided, since increased skin pigmentation can provide a defense against ultraviolet (UV) light-induced DNA damage, including melanoma.

Skin and Pigmentation

In addition to cooperating with each other, cutaneous epithelial cells must interact with nonepithelial cell types to produce the skin's complex features. Perhaps the most striking example of these heterotypic interactions can be found in the process of pigmentation, which requires an elaborate system of direct connections between epithelial cells and melanocytes. In the multi-step pigmentary process, melanocytes first synthesize melanin in specialized cytoplasmic organelles (melanosomes) that migrate to the tips of the dendrites. The pigment-rich melanosomes are then transferred to epithelial cells, most likely through phagocytosis. Once inside the epithelial cells, the melanin is either stored or degraded, thus determining the intensity of pigmentation. Typically, one melanocyte provides pigment to many epithelial cells, creating an "epithelial-melanin unit", and human skin develops these units in both the epidermis and hair follicles. In contrast, mice lack pigment in most regions of the epidermis, though these animals are similar (if not identical) to humans in most other features of the pigmentary system. In mouse embryos, melanocyte precursors (melanoblasts) colonize the epidermis, but epithelial-melanin units fail to form. Instead, as the hair follicles develop, the melanoblasts migrate into these appendages, eventually disappearing from the epidermis.

From genetic and molecular studies has come significant progress in understanding how melanocytes develop. Nonetheless, little is known about the interaction of melanocytes and epithelial cells. Presumably, these cell types signal to each other during their association, thereby ensuring the proper and successful transfer of pigment. Based on simple observation of the skin, there is clearly specificity in melanocytic-epithelial interactions. For example, though melanoblasts colonize both human and murine epidermis, only human epidermis retains these cells. Hence, human keratinocytes must emit signals or possess interactive abilities that are lacking in their murine counterparts. Similarly, within the hair bulb, melanocytes are in close proximity to seven different types of epithelial cells (three types of differentiating hair cells, three types of differentiating inner root sheath cells, and the undifferentiated matrix cells). Yet, the melanocytes transfer pigment to only two cell types—the differentiating precursors of the hair cortex and medulla. Since the melanocytes provide pigment to some neighbors and not others, the pigment recipients must differ with the surrounding cells in some way. Thus, the question arises as to how melanocytes identify their target cells.

A knock-in construct was used to introduce the β-galactosidase gene into the Foxn1 gene. β-gal expression was monitored in cells to determine where the Foxn1 promoter was active. Based on this analysis, Foxn1 expression is found in cells of the superbasal layer, cells of the hair cortex, and in the outer and inner root sheaths, where it may be expressed in melanocyte stem cells.

Foxn1

Foxn1 (previously named Whn) is the product of the mouse nude locus. Mice carrying loss-of-function mutations in this protein display the nude phenotype, which is characterized by structural defects in the epidermis, the failure to produce visible hair, the inability of females to nourish their pups, and the absence of a thymus. Foxn1 includes a winged-helix DNA binding domain and a negatively-charged domain capable of activating transcription. Accordingly, Foxn1 protein may function as a transcriptional activator.

Exemplary Foxn1 amino acid and nucleotide sequences (including human and other mammalian species) are available, e.g., from Schorpp et al. (1997) Immunogenetics 46 (6), 509-515 and GENBANK® entry O15353 [GI:13124629]. The protein has a winged-helix DNA binding domain located at about amino acids 271 to 367 or about 271 to 349. Exemplary fragments of the human Foxn1 protein include fragments that include, or consist of, about amino acids 1-270, 10-180, 271-367, 271-349, 350-648, 368-648, 400-550, and 500-640. Such fragments can be fused to heterologous amino acids, e.g., sequences other than Foxn1.

A Foxn1 sequence may be at least 70, 75, 80, 85, 90, 92, 94, 95, 96, 97, 98, or 99% identical to a human Foxn1 sequence, and may have biological activity, e.g., in a mouse model (e.g., nude mouse) or a human cell.

Other proteins may function in the Foxn1 signalling pathway. Such proteins include proteins encoded by genes whose transcription is directly regulated by Foxn1 (e.g., as determined using a microarray) and proteins and other factors that modulate Foxn1 activity. For example, wnt proteins can regulate expression of Foxn1. See, e.g., Balciunaite G et al. (2002) Nat Inmunol. 3(11):1102-8.

Krt5-Foxn1 Mice

Transgenic mice that express Foxn1 from the keratin 5 (Krt5) promoter are described herein. In the skin, this promoter targets Foxn1 to epithelial cells that act as the progenitors of differentiated structures or cell types. In the epidermis, the transgene is expressed in basal keratinocytes, which generally lack endogenous Foxn1. As expected, the transgene affects epidermal growth and differentiation, though these effects are mild in most animals. In wild-type mice, the epidermis progressively thins following birth, as the coat grows in and provides protection from the environment. In the Krt5-Foxn1 mice, the epidermis thins more rapidly, and many basal keratinocytes display morphological features of differentiation. Thus, the Krt5-Foxn1 transgene may increase the propensity of keratinocytes to differentiate, consistent with our model of Foxn1 function.

Unexpectedly, the Krt5-Foxn1 mice also display changes in pigmentation. In transgenic skin, melanin accumulates within the epidermis, with much, if not most, of the pigment located in basal keratinocytes. Consistent with this melanization, the transgenic epidermis also exhibits high numbers of melanocytes, and as in human skin, the pigment cells are located primarily in the basal layer. Thus, the Krt5-Foxn1 transgene transforms the epidermis into a pigmented tissue, apparently converting the keratinocytes into melanocyte target cells.

At the macroscopic level, most Krt5-Foxn1 mice appear normal, though animals occasionally display runting, flaky skin, and sparse hair. Despite the numerous melanocytes in the epidermis, the transgenic coat shows no abnormalities in its pigmentation. Thus, the transgene does not deplete the hair of melanin or prevent the migration of melanocytes into the hair follicles. Moreover, since most transgenics possess a well-formed skin, the pigment phenotype does not result from a general disruption of skin development. Rather, the transgene specifically reorganizes and reshapes the pigment cell population. As a result, the transgenics possess a human-like pigmentary system, with melanocytes populating the epidermis and hair follicles.

These observations indicate a role for Foxn1 in pigmentation. This role was surprising since nude mice do not display any obvious pigment-related defects. In nude hair follicles, melanocytes enter the hair bulb, adopt their correct location, and appear to produce normal levels of melanin. Thus, during follicle development, Foxn1 is not essential for the migration or differentiation of pigment cells. Rather, as an epithelial transcription factor, Foxn1 may regulate the formation of epithelial-melanin units. In wild-type hair follicles, Foxn1 is most abundant in the differentiating precursors of the cortex, which receive pigment from melanocytes. To a lesser extent, Foxn1 is also detected in the differentiating medulla, the other melanized structure of the hair. Thus, as a hair grows and becomes pigmented, Foxn1 is present in the melanocyte target cells. Taking our results together, we propose that Foxn1 promotes the functional association of melanocytes and epithelial cells. Specifically, Foxn1 may identify a cell as a melanocyte target or stimulate the intercellular contacts required for pigment transfer.

In summary, it was unexpected that a mammal whose genome comprises a Foxn1 transgene expressed in basal epithelial cells of the epidermis or hair follicles would have altered skin appearance, e.g., pigmentation. Although not bound by theory, it is hypothesized that Foxn1 acts a regulatory link or nexus, coordinating the growth, differentiation, and pigmentation of an epithelium.

Agents

Agents and test agents to be used in the methods described herein include crude or partially or substantially purified extracts of organic sources, e.g., botanical (e.g., herbal) and algal extracts, inorganic elements or compounds, as well as partially or substantially purified or synthetic agents, e.g., small molecules, polypeptides, antibodies, and polynucleotides, and libraries of these. Preferably, the agent is other than FGF2.

Chemical Libraries. In one example, combinatorial chemical libraries can be produced that sample chemical compounds that are structurally or chemically related. For example, a scaffold is selected based on information about the known agonist. Then various positions on the scaffold are modified in combination to produce a large number of different compounds. The diversity of particular positions can be precisely controlled.

Methods for producing chemical libraries are well known. See, for example, Cox et al. (2000) Prog Med Chem 37:83; Sternson (2001) Org Lett 3(26):4239-42; Tam et al. (1998) J. Am Chem. Soc. 120:8565; 1: Floyd et al. (1999) Prog Med Chem. 36:91-168.; Rohrer et al. (1998) Science.;282(5389):737-40; Komarov et al. (1999) Science. 285(5434):1733-7; Mayer et al. (1999) Science. 286(5441):971-4.

Members of a chemical library can be tagged. In such libraries, the identity and composition of each member of the library is uniquely specified by the label or "tag" which is physically associated with it and hence the compositions of those members that bind to a given target or that have a particular activity are specified directly (see, e.g., Ohlmeyer et al., 1993, Proc. Natl. Acad. Sci. USA 90:10922-10926; Brenner et al., 1992, Proc. Natl. Acad. Sci. USA 89:5381-5383; Lerner et al., PCT Publication No. WO 93/20242). In other examples of such libraries, the library members are created by step wise synthesis protocols accompanied by complex record keeping, complex mixtures are screened, and deconvolution methods are used to elucidate which individual members were in the sets that had activity (e.g., binding or biological activity), and hence which synthesis steps produced the members and the composition of individual members (see, e.g., Erb et al., 1994, Proc. Natl. Acad. Sci. USA 91:11422-11426).

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, Int. J. Pept. Prot. Res. 37:487-493 (1991) and Houghton et al., Nature 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., Proc. Nat. Acad. Sci. USA 90:6909-6913 (1993)), vinylogous polypeptides (Hagihara et al., J. Amer. Chem. Soc. 114:6568 (1992)), nonpeptidal peptidomimetics with glucose scaffolding (Hirschmann et al., J. Amer. Chem. Soc. 114:9217-9218 (1992)), analogous organic syntheses of small compound libraries (Chen et al., J. Amer. Chem. Soc. 116:2661 (1994)), oligocarbamates (Cho et al., Science 261:1303 (1993)), and/or peptidyl phosphonates (Campbell et al., J. Org. Chem. 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., Nature Biotechnology, 14(3): 309-314 (1996) and PCT/US96/10287), carbohydrate libraries (see, e.g., Liang et al., Science, 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

In one embodiment, the invention provides solid phase based in vitro assays in a high throughput format, where the target cell or tissue is attached to a solid phase substrate. In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 96 modulators. If 1536 well plates are used, then a single plate can easily assay from about 100- about 1500 different compounds. It is possible to assay many plates per day; assay screens for up to about 6,000, 20,000, 50,000, or 100,000 or more different compounds are possible using the integrated systems of the invention.

Methods of Identifying an Agent Modulating Foxn1 Expression or Foxn1 Activity or Level Numerous methods exist for evaluating whether an agent alters Foxn1 expression or Foxn1 activity or level. In one embodiment, the ability of a test agent to modulate (e.g., increase or decrease) (e.g., permanently or temporarily) expression from a Foxn1 promoter is evaluated by e.g., routine reporter (e.g., LacZ or GFP) transcription assay. For example, a cell or transgenic animal whose genome comprises a reporter gene operably linked to a Foxn1 promoter, can be contacted with a test agent, and the ability of the test agent to increase or decrease reporter activity is indicative of the ability of the agent to modulate pigmentation. In another embodiment, the ability of a test agent to modulate Foxn1 expression, or Foxn1 activity or level is evaluated in a transgenic animal, for example, the transgenic animal described herein.

The effect of a test agent on Foxn1 expression or Foxn1 activity or level may also be evaluated using a melanocyte migration assay (see, e.g., Santiago et al., 2000, Development 129:3621-32).

The effect of a test agent on Foxn1 expression or Foxn1 activity or level may also be evaluated in a cell, cell lysate, co-culture comprising a melanocyte and a non-melanocyte (See e.g., Yoon et al. (2003) Pigment Cell Res. 16:159; Lei et al. (2002) Anal Biochem. 305:260; Hedley et al. (2002) Pigment Cell Res. 15:49; Virador et al. (1999) Anal Biochem. 270:207), or subject, preferably a non-human experimental mammal, and more preferably a rodent (e.g., a rat, mouse, rabbit), or explant (e.g., skin) thereof. Methods of assessing Foxn1 expression are well know in the art, e.g., Northern analysis, ribonuclease protection assay, reverse transcription-polymerase chain reaction (RT-PCR) or RNA in situ hybridization (see, e.g., Sambrook et al. *Molecular Cloning: A Laboratory Manual* (3$^{rd}$ ed. 2001)). The level of Foxn1 may be monitored by, e.g., Western analysis, immunoassay, or in situ hybridization. Foxn1 activity (e.g. altered promoter binding and/or transcription activity) may be determined by, e.g., electrophoretic mobility shift assay, DNA footprinting or reporter gene assay. Preferably, the effect of a test agent on Foxn1 expression or Foxn1 activity or level is observed as a change in pigmentation of the cell, cell extract, co-culture, explant or subject. More preferably, the effect of a test agent on Foxn1 expression or Foxn1 activity or level is evaluated on a transgenic cell or non-human animal, or explant or cell derived therefrom, having altered pigmentation as compared to a wild-type cell or non-human animal, or explant or cell derived therefrom.

The test agent may be administered to a cell, cell extract, explant or subject expressing a transgene comprising the Foxn1 promoter fused to LacZ. (See, e.g., Cunliffe et al. (2002) *Mamm Genome* 13:245 and Schorpp et al. (1997) *Immunogenetics* 46:509 characterizing the promoter of Foxn1/whn. See, e.g., Nehls et al. (1996) *Science* 272:886 and Lee et al. (1999) *Dev Biol.* 208:362 placing the beta-galactosidase reporter gene under control of the whn promoter.) Enhancement or inhibition of transgene, e.g., a reporter, e.g., LacZ or GFP, transcription, as a result of an effect of the test agent on the Foxn1 promoter or factors regulating transcription from the Foxn1 promoter, may be easily observed as a change in color. Reporter transcript levels, and thus Foxn1 promoter activity, may be monitored by established methods, e.g., Northern analysis, ribonuclease protection assay, reverse transcription-polymerase chain reaction (RT-PCR) or RNA in situ hybridization (see, e.g., Cuncliffe et al. (2002) *Mamm Genome* 13:245). Agents may be evaluated using a cell-free system, e.g., an environment comprising the Foxn1 promoter-reporter transgene (e.g., Foxn1 promoter-LacZ transgene), transcription factors binding the Foxn1 promoter, a crude cell lysate or nuclear extract, and the test agent (e.g., an agent described herein), wherein an effect of the agent on Foxn1 promoter activity is detected as a color change.

Foxn1 is a member of the forkhead family of transcription factors containing a winged-helix domain (see, e.g., Schorpp et al. (1997) *Immunogenetics* 46:509). Members of this family share a highly conserved stretch of 100 amino acids containing a modified helix-turn-helix located in the middle of the protein. The similarities of these proteins, and the helix-turn-helix motif in particular, may be used to generate computer predictions of agents interacting with Foxn1.

Measurement of Pigmentation

The effect of an agent on skin pigmentation can be evaluated qualitatively, e.g., by visual inspection. Qualitative indicia include a change in skin color, tone, hue, and/or shade. An optional, reference index of, e.g., colors or hues, may facilitate a qualitative assessment. All, most or some of the cells and/or areas of the explant or subject treated with the test agent may be affected. A treated cell, explant or subject may be compared with an untreated cell, explant or subject. More preferably, a treated region and an untreated region of the same cell culture, explant or subject are compared.

Co-culture systems of melanocytes and non-melanocytes can also be used to assay melanocyte function and pigmentation (See e.g., Yoon et al. (2003) Pigment Cell Res. 16:159; Lei et al. (2002) Anal Biochem. 305:260; Hedley et al. (2002) Pigment Cell Res. 15:49; Virador et al. (1999) Anal Biochem. 270:207).

The effect of an agent on pigmentation may also be evaluated quantitatively, e.g., by microscopic or computer-assisted measurements of pigmentation. The number of melanosomes, size of melanosomes and redistribution of melanosomes in keratinocytes may be determined. Proliferation of and/or melanin synthesis of melanocytes may be ascertain by, e.g., melanocyte tyrosinase activity by, e.g., tyrosine hydroxylase (see, e.g., U.S. Pub. application 20020192738) and/or [$^{14}$C]melanin assays. Reflectance spectrophotometry and reflectance colorimetry/spectroscopy may also be used. The evaluation may include entering a value for the evaluation, e.g., a value for the extent or type of change in pigmentation into a database or other record.

The party measuring and/or recording pigmentation may be the care provider, the subject or another party.

Transgenic Animals

Detailed methods for generating non-human transgenic animals are described herein and in the section entitled "Examples" below. Such methods can involve introducing the nucleic acid of interest, e.g. Foxn1, into the germ line of a non-human animal to make a transgenic animal. Although rodents, e.g., rats, mice, rabbits and guinea pigs, are preferred, other non-human animals can be used. For example, one or several copies of the nucleic acid of interest may be incorporated into the DNA of a mammalian embryo by standard transgenic techniques (see, e.g., Nagy et al. *Manipulating the Mouse Embryo: A Laboratory Manual* (3rd ed. 2003)). A protocol for the production of a transgenic rat can be found in Bader et al. (1996) *Clin Exp Pharmacol Physiol Suppl.* 3:S81-7.

Transgenic mice containing a Krt5-Foxn1 transgene may be generated by established methods. Other expression control sequences may direct expression of Foxn1, or a functional fragment or variant thereof, e.g., the helix-turn-helix motif or the transcriptional activation domain, to a cell type substantially lacking endogenous Foxn1, e.g., the Keratin 14 promoter (Sinha et al. (2000) *Mol Cell Biol.* 20:2543; Guo et al. (1993) *EMBO J.* 12:973) or the loricrin promoter (Jang et al. (2002) *J Biol Chem.* 277:42268; DiSepio et al. (1999) *Differentiation* 64:225). Other polyadenylation sequences from, e.g., Foxn1n, Krt5 or Krt14, may be used (see e.g., Schorpp et al. (1997) *Immunogenetics* 46:509). Preferably, the expression control sequence directs Foxn1 expression to basal epithelial cells of the epidermis or hair follicles.

Transfected Cell Lines

Genetically engineered cells, tissues, or animals can be obtained from a cell, e.g., an embryonic stem cell or a keratinocyte, into which a nucleic acid of interest, e.g., a nucleic acid which encodes a protein, e.g., Foxn1, has been introduced. A nucleic acid of interest, or a vector, e.g., a plasmid, including the nucleic acid of interest, can be introduced into a cell, e.g. a prokaryotic or eukaryotic cell, via conventional transformation or transfection techniques, e.g., calcium phosphate or calcium chloride co-precipitation, DEAE-dextrane-mediated transfection, lipofection, electroporation or viral infection. Suitable vectors, cells, methods for transforming or transfecting host cells and methods for cloning the nucleic acid of interest into a vector can be found in, e.g., Sambrook et al. *Molecular Cloning: A Laboratory Manual* (3rd ed. 2001).

Administration

The agent may be administered systemically or locally, e.g., topically. Topical administration with an agent described herein is the preferred route of administration. For topical application, the compositions of the present invention can include a medium compatible with a cell, explant or subject. Such topical pharmaceutical compositions can exist in many forms, e.g., in the form of a solution, cream, ointment, gel, lotion, shampoo, soap or aerosol. A wide variety of carrier materials can be employed in the pigment modulating composition of this invention such as alcohols, aloe vera gel, allantoin, glycerine, vitamin A and E oils, mineral oils, and polyethylene glycols. Other additives, e.g., preservatives, fragrance, sunscreen, or other cosmetic ingredients, can be present in the composition.

A preferred vehicle for topical delivery is liposomes. Liposomes can be used to carry and deliver an agent, e.g., a agent described herein, e.g., Foxn1, into a cell. Detailed guidance can be found in, e.g., Yarosh et al. (2001) Lancet 357: 926 and Bouwstra et al. (2002) Adv. Drug Deliv. Rev. 54 Suppl 1: S41

For systemic administration the agent may be administered via the orally route or the parenteral route, including subcutaneously, intraperitoneally, intramuscularly, intravenously or other route. For local administation, they are administered topically, transdermally, transmucosally, intranasally or other route. A cell may be contacted extracellularly or intracellularly with the agent, e.g., by microinjection or tranfection. The agent may be applied and removed immediately, applied and not removed, and/or repeatedly applied with constant, increasing or decreasing frequency and/or at increasing or decreasing doses or concentrations. More than one route of administration may be used simultaneously, e.g., topical administration in association with oral administration. Examples of parenteral dosage forms include aqueous solutions of the active agent, in a isotonic saline, 5% glucose or other well-known pharmaceutically acceptable excipient. Solubilizing agents such as cyclodextrins, or other solubilizing agents well-known to those familiar with the art, can be utilized as pharmaceutical excipients for delivery of the pigment modulating composition.

The composition may be provided as, e.g., a cosmetics, a medication or a skin care product. The composition can also be formulated into dosage forms for other routes of administration utilizing conventional methods. A pharmaceutical composition can be formulated, for example, in dosage forms for oral administration as a powder or granule, or in a capsule, a tablet (each including timed release and sustained release formulations), or a gel seal, with optional pharmaceutical carriers suitable for preparing solid compositions, such as vehicles (e.g., starch, glucose, fruit sugar, sucrose, gelatin and the like), lubricants (e.g., magnesium stearate), disintegrators (e.g., starch and crystalline cellulose), and binders (e.g., lactose, mannitol, starch and gum arabic). When the composition is an injection, for example, solvents (e.g., distilled water for injection), stabilizers (e.g., sodium edetate), isotonizing agents (e.g., sodium chloride, glycerine and mannitol), pH adjusting agents (e.g., hydrochloric acid, citric acid and sodium hydroxide), suspending agents (e.g., methyl cellulose) and the like may be used.

The pigmentation modulating agent may contain other pharmaceutical ingredients, e.g., an antitumor drug, an antimicrobial agent, or a dermatological agent.

Subjects in Need of Altered Skin Pigmentation and Methods of Treatment

Numerous subjects are in need of altered skin pigmentation. Subjects with skin pigmentation pathologies, such as vitiligo, chloasma and ephelis, require altered skin pigmentation. Those exposed to ultraviolet light, especially for prolonged periods (e.g., lifeguards), are in need of increased skin pigmentation. Persons seeking darker skin (e.g. a "tan") without the hazards posed by exposure to the sun or ultraviolet rays require altered skin pigmentation. The identification of a subject in need of altered pigmentation can be performed by the subject, a health care provider, or another party.

The subject may be supplied with a composition affecting a component of the Foxn1 signal transduction pathway by a health care provider, cosmetics retailer or another party. Instructions for using a composition affecting a component of the Foxn1 signal transduction pathway may be provided by a health care provider, cosmetics retailer or another party. A kit comprising a composition affecting a component of the Foxn1 signal transduction pathway and instructions for using the composition may be provided by a health care provider, cosmetics retailer or another party. Preferably the component of the Foxn1 pathway is Foxn1, or a fragment or variant thereof.

Pharmacokinetic Properties and Therapeutic Activity

Modifications can be made to a protein that result in pharmacokinetic properties of the protein which are desirable for use in protein therapy. For example, such modifications can result in longer circulatory half-life, an increase in cellular uptake, improved distribution to targeted tissues, a decrease in clearance and/or a decrease of immunogenicity. Several art-recognized approaches useful to optimize the therapeutic activity of a protein, e.g., a therapeutic protein described herein, e.g., a Foxn1 polypeptide, are summarized below.

Expression System

For recombinant proteins, the choice of expression system can influence pharmacokinetic characteristics. Differences between expression systems in post-translational processing lead to recombinant proteins of varying molecular size and charge, which can affect circulatory half-life, rate of clearance and immunogenicity, for example. The pharmacokinetic properties of the protein may be optimized by the appropriate selection of an expression system, such as selection of a bacterial, viral, or mammalian expression system. Exemplary mammalian cell lines useful in expression systems for therapeutic proteins are Chinese hamster ovary, (CHO) cells, the monkey COS-1 cell line and the CV-1 cell line.

Chemical Modification

A protein can be chemically altered to enhance the pharmacokinetic properties while maintaining activity. The protein can be covalently linked to a variety of moieties, altering the molecular size and charge of the protein and consequently its pharmacokinetic characteristics. The moieties are preferably non-toxic and biocompatible. In one embodiment, polyethylene glycol (PEG) can be covalently attached to the protein (PEGylation). PEG is a class of polymers comprised of repeating ethylene oxide subunits with terminal hydroxyl groups. A variety of PEG molecules are known and/or commercially available (See, e.g., Sigma-Aldrich catalog). PEG molecules are available in various lengths, molecular weights, and substitution patterns, and may be linear or branched. PEG is attached to the protein via an activated terminal hydroxyl group; preferably, the hydroxyl group is activated as an ester, carbonate, aldehyde or tresylate. The activated hydroxyl reacts with nucleophilic groups on the protein, forming a linkage between the protein and PEG. Often the nucleophilic group is the amino group of a lysine or the N-terminus of the protein. One or multiple chains of PEG may be attached to the protein. The choice of site(s) and functionality of the linkage of PEGylation and the choice of PEG molecule can be optimized to achieve the desired pharmacokinetic properties. PEGylation can increase the stability of the protein, decrease immunogenicity by steric masking of epitopes, and improve half-life by decreasing glomerular filtration. (See, e.g., *Poly(ethylene glycol): chemistry and biological applications*, Harris and Zalipsky, eds., ACS Symposium Series, No. 680, 1997; Harris et al., Clinical Pharmacokinetics 40:7, 485-563 (2001)). Examples of therapeutic proteins administered as PEG constructs include Adagen (PEG-ADA) and Oncospar (Pegylated asparaginase). In another embodiment, the protein can be similarly linked to oxidized dextrans via an amino group. (See Sheffield, 2001, Current Drug Targets—Cardiovas. & Haemat. Dis. 1:1, 1-22). In yet another embodiment, conjugation of arginine oligomers to cyclosporin A can facilitates topical delivery (Rothbard et al., 2000, Nat Med. 6(11):1253-7).

Furthermore, the therapeutic protein may be chemically linked to another protein. The therapeutic protein can be cross-linked carrier protein to form a larger molecular weight complex with longer circulatory half-life and improved cellular uptake. In one embodiment, the carrier protein can be a serum protein, such as albumin. The therapeutic protein can be attached to one or more albumin molecules via a bifunctional cross-linking reagent. The cross-linking reagent may be homo- or heterofunctional. In another embodiment, the therapeutic protein can cross-link with itself to form a homodimer, trimer, or higher analog. Again, either heterobifunctional or homobifunctional cross-linking reagents can be used to form the dimers or trimers. (See Stykowski et al., Proc. Natl. Acad. Sci. USA, 95, 1184-1188 (1998)). Increasing the molecular weight and size of the therapeutic protein through dimerization or trimerization can decrease clearance.

Modification of Protein Formulation

The formulation of the protein may also be changed. The therapeutic protein can be formulated in a carrier system.

The carrier can be a colloidal system. The colloidal system can be liposome, a phospholipid bilayer vehicle. In one embodiment, the therapeutic protein is encapsulated in a liposome while maintaining protein integrity. As one skilled in the art would appreciate, there are a variety of methods to prepare liposomes. (See Lichtenberg, D., et al., Methods Biochem Anal, 33:337-462 (1988), LIPOSOME TECHNOLOGY Anselem, S. et al., CRC Press, 1993). Liposomes can be prepared from an assortment of phospholipids varying in size and substitution, and may also contain additional components with low toxicity, such as cholesterol. The liposome can be formulated and isolated in a variety of shapes and sizes. Additionally, moieties may attached to the surface of the liposome to further enhance the pharmacokinetic properties of the carrier. The moieties may be attached to phospholipid or cholesterol molecules, and the percentage of the moiety incorporated on the surface may be adjusted for optimal liposome stability and pharmacokinetic characteristics. One embodiment comprises a liposome with poly-ethylene glycol (PEG) added to the surface. Liposomal formulations can delay clearance and increase cellular uptake. (See Reddy, K. R., Annals of Pharmacotherapy, 34:7/8, 915-923 (2000)).

The carrier can also be a polymer, e.g., a biodegradable, biocompatible polymer matrix. In one embodiment, the therapeutic protein can be embedded in the polymer matrix while maintaining protein integrity. The polymer may be natural, such as polypeptides, proteins or polysaccharides, or synthetic, such as poly($\alpha$-hydroxy) acids. Examples include carriers made of, e.g., collagen, fibronectin, elastin, cellulose acetate, cellulose nitrate, polysaccharide, fibrin, gelatin, and combinations thereof. In one embodiment, the polymer is poly-lactic acid (PLA) or copoly lactic/glycolic acid (PGLA). The polymeric matrices can be prepared and isolated in a variety of forms and sizes, including microspheres and nanospheres. Polymer formulations can lead to prolonged duration of therapeutic effect. (See Reddy, K. R., Annals of Pharmacotherapy, 34:7/8, 915-923 (2000)). A polymer formulation for human growth hormone (hGH) has been used in clinical trials. (See Kozarich, J. W., Rich, D. H., Chemical Biology 2:548-552 (1998)).

Examples of polymer microsphere sustained release formulations are described in PCT publication WO 99/15154 (Tracy et al.), U.S Pat. Nos. 5,674,534 and 5,716,644 (both to Zale et al.), PCT publication WO 96/40073 (Zale et al.), and PCT publication WO 00/38651 (Shah et al.). U.S. Pat. Nos. 5,674,534 and 5,716,644 and PCT publication WO 96/40073 describe a polymeric matrix containing particles of erythropoietin that are stabilized against aggregation with a salt.

Gene Therapy

The nucleic acids described herein, e.g., an antisense nucleic acid described herein, or Foxn1 polypeptide encoding nucleic acid, can be incorporated into a gene construct to be used as a part of a gene therapy protocol to deliver nucleic acids encoding either an agonistic or antagonistic form of an agent described herein. The invention features expression vectors for in vivo transfection and expression of a Foxn1 polypeptide described herein in particular cell types. Expression constructs of such components may be administered in any biologically effective carrier, e.g. any formulation or composition capable of effectively delivering the component gene to cells in vivo. Approaches include insertion of the subject gene in viral vectors including recombinant retroviruses, adenovirus, adeno-associated virus, lentivirus, and herpes simplex virus-1, or recombinant bacterial or eukaryotic plasmids. Viral vectors transfect cells directly; plasmid DNA can be delivered with the help of, for example, cationic liposomes (lipofectin) or derivatized (e.g. antibody conjugated), polylysine conjugates, gramacidin S, artificial viral envelopes or other such intracellular carriers, as well as direct injection of the gene construct or $CaPO_4$ precipitation carried out in vivo.

A preferred approach for in vivo introduction of nucleic acid into a cell is by use of a viral vector containing nucleic acid, e.g. a cDNA. Infection of cells with a viral vector has the advantage that a large proportion of the targeted cells can receive the nucleic acid. Additionally, molecules encoded within the viral vector, e.g., by a cDNA contained in the viral vector, are expressed efficiently in cells which have taken up viral vector nucleic acid.

Retrovirus vectors and adeno-associated virus vectors can be used as a recombinant gene delivery system for the transfer of exogenous genes in vivo, particularly into humans. These vectors provide efficient delivery of genes into cells, and the transferred nucleic acids are stably integrated into the chromosomal DNA of the host. The development of specialized cell lines (termed "packaging cells") which produce only replication-defective retroviruses has increased the utility of retroviruses for gene therapy, and defective retroviruses are characterized for use in gene transfer for gene therapy purposes (for a review see Miller, A. D. (1990) Blood 76:271). A replication defective retrovirus can be packaged into virions which can be used to infect a target cell through the use of a helper virus by standard techniques. Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14 and other standard laboratory manuals. Examples of suitable retroviruses include pLJ, pZIP, pWE and pEM which are known to those skilled in the art. Examples of suitable packaging virus lines for preparing both ecotropic and amphotropic retroviral systems include *Crip, *Cre, *2 and *Am. Retroviruses have been used to introduce a variety of genes into many different cell types, including epithelial cells, in vitro and/or in vivo (see for example Eglitis, et al. (1985) Science 230:1395-1398; Danos and Mulligan (1988) Proc. Natl. Acad. Sci. USA 85:6460-6464; Wilson et al. (1988) Proc. Natl. Acad. Sci. USA 85:3014-3018; Armentano et al. (1990) Proc. Natl. Acad. Sci. USA 87:6141-6145; Huber et al. (1991) Proc. Natl. Acad. Sci. USA 88:8039-8043; Ferry et al. (1991) Proc. Natl. Acad. Sci. USA 88:8377-8381; Chowdhury et al. (1991) Science 254:1802-1805; van Beusechem et al. (1992) Proc. Natl. Acad. Sci. USA 89:7640-7644; Kay et al. (1992) Human Gene Therapy 3:641-647; Dai et al. (1992) Proc. Natl. Acad. Sci. USA 89:10892-10895; Hwu et al. (1993) J. Immunol. 150:4104-4115; U.S. Pat. No. 4,868,116; U.S. Pat. No. 4,980,286; PCT Application WO 89/07136; PCT Application WO 89/02468; PCT Application WO 89/05345; and PCT Application WO 92/07573).

Another viral gene delivery system useful in the present invention utilizes adenovirus-derived vectors. The genome of an adenovirus can be manipulated such that it encodes and expresses a gene product of interest but is inactivated in terms of its ability to replicate in a normal lytic viral life cycle. See, for example, Berkner et al. (1988) BioTechniques 6:616; Rosenfeld et al. (1991) Science 252:431-434; and Rosenfeld et al. (1992) Cell 68:143-155. Suitable adenoviral vectors derived from the adenovirus strain Ad type 5 dl324 or other strains of adenovirus (e.g., Ad2, Ad3, Ad7 etc.) are known to those skilled in the art. Recombinant adenoviruses can be advantageous in certain circumstances in that they are not capable of infecting nondividing cells and can be used to infect a wide variety of cell types, including epithelial cells (Rosenfeld et al. (1992) cited supra). Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) J. Virol. 57:267).

Yet another viral vector system useful for delivery of the subject gene is the adeno-associated virus (AAV). Adeno-associated virus is a naturally occurring defective virus that requires another virus, such as an adenovirus or a herpes virus, as a helper virus for efficient replication and a productive life cycle. (For a review see Muzyczka et al. (1992) Curr. Topics in Micro. and Inmunol. 158:97-129). It is also one of the few viruses that may integrate its DNA into non-dividing cells, and exhibits a high frequency of stable integration (see for example Flotte et al. (1992) Am. J. Respir. Cell. Mol. Biol. 7:349-356; Samulski et al. (1989) J. Virol. 63:3822-3828; and McLaughlin et al. (1989) J. Virol. 62:1963-1973). Vectors containing as little as 300 base pairs of AAV can be packaged and can integrate. Space for exogenous DNA is limited to about 4.5 kb. An AAV vector such as that described in Tratschin et al. (1985) Mol. Cell. Biol. 5:3251-3260 can be used to introduce DNA into cells. A variety of nucleic acids 10 have been introduced into different cell types using AAV vectors (see for example Hermonat et al. (1984) Proc. Natl. Acad. Sci. USA 81:6466-6470; Tratschin et al. (1985) Mol. Cell. Biol. 4:2072-2081; Wondisford et al. (1988) Mol. Endocrinol. 2:32-39; Tratschin et al. (1984) J. Virol. 51:611-619; and Flotte et al. (1993) J. Biol. Chem. 268:3781-3790).

An exemplary method for preparing an adenoviral vector that encodes a Foxn1 polypeptide or a fragment thereof includes using the ADEASY™ vector (available, e.g., from Q-BIO-GENE, Irvine Calif.). See, e.g., He et al. (1998) Proc Natl Acad Sci USA. 95(5):2509-14. A nucleic acid segment encoding Foxn1 or a fragment thereof operably linked to a promoter can be cloned into a plasmid at a site located between left and right recombination sites. This plasmid can then be recombined with a transfer vector that includes adenoviral genes to produce a recombinant adenoviral nucleic acid that can be used to produce virus that can deliver Foxn1.

In addition to viral transfer methods, such as those illustrated above, non-viral methods can also be employed to cause expression of a nucleic acid agent described herein (e.g., a Foxn1 polypeptide encoding nucleic acid) in the tissue of a subject. Most nonviral methods of gene transfer rely on normal mechanisms used by mammalian cells for the uptake and intracellular transport of macromolecules. In preferred embodiments, non-viral gene delivery systems of the present invention rely on endocytic pathways for the uptake of the subject gene by the targeted cell. Exemplary gene delivery systems of this type include liposomal derived systems, polylysine conjugates, and artificial viral envelopes. Other embodiments include plasmid injection systems such as are described in Meuli et al. (2001) J Invest Dermatol. 116(1): 131-135; Cohen et al. (2000) Gene Ther 7(22):1896-905; or Tam et al. (2000) Gene Ther 7(21):1867-74.

In a representative embodiment, a gene encoding an agent described herein, e.g., Foxn1, can be entrapped in liposomes bearing positive charges on their surface (e.g., lipofectins) and (optionally) which are tagged with antibodies against cell surface antigens of the target tissue (Mizuno et al. (1992) No Shinkei Geka 20:547-551; PCT publication WO91/06309; Japanese patent application 1047381; and European patent publication EP-A-43075).

In clinical settings, the gene delivery systems for the therapeutic gene can be introduced into a patient by any of a number of methods, each of which is familiar in the art. For instance, a pharmaceutical preparation of the gene delivery system can be introduced systemically, e.g. by intravenous injection, and specific transduction of the protein in the target cells occurs predominantly from specificity of transfection provided by the gene delivery vehicle, cell-type or tissue-type expression due to the transcriptional regulatory sequences controlling expression of the receptor gene, or a combination thereof. In other embodiments, initial delivery of the recombinant gene is more limited with introduction into the animal being quite localized. For example, the gene delivery vehicle can be introduced by catheter (see U.S. Pat. No. 5,328,470) or by stereotactic injection (e.g. Chen et al. (1994) PNAS 91: 3054-3057).

The pharmaceutical preparation of the gene therapy construct can consist essentially of the gene delivery system in an acceptable diluent, or can comprise a slow release matrix in which the gene delivery vehicle is imbedded. Alternatively, where the complete gene delivery system can be produced in tact from recombinant cells, e.g. retroviral vectors, the pharmaceutical preparation can comprise one or more cells which produce the gene delivery system.

Cell Therapy

An agent described herein for modulating, e.g., increasing Foxn1 signaling, e.g., a Foxn1 polypeptide or active fragment thereof, can also be increased in a subject by introducing into a cell, e.g., a skin cell such as a keratinocyte, a nucleotide sequence that encodes a Foxn1 polypeptide. The nucleotide sequence can be a Foxn1 encoding sequence or active fragment thereof, and any of: a promoter sequence, e.g., a promoter sequence from a Foxn1 gene or from another gene; an enhancer sequence, e.g., 5' untranslated region (UTR), e.g., a 5' UTR from a Foxn1 gene or from another gene, a 3' UTR, e.g., a 3' UTR from a Foxn1 gene or from another gene; a polyadenylation site; an insulator sequence; or another sequence that modulates the expression of Foxn1. The cell can then be introduced into the subject.

Primary and secondary cells to be genetically engineered can be obtained from a variety of tissues and include cell types which can be maintained and propagated in culture. For example, primary and secondary cells include adipose cells, fibroblasts, keratinocytes, epithelial cells (e.g., mammary epithelial cells, intestinal epithelial cells), endothelial cells, glial cells, neural cells, formed elements of the blood (e.g., lymphocytes, bone marrow cells), muscle cells (myoblasts) and precursors of these somatic cell types. Primary cells are preferably obtained from the individual to whom the genetically engineered primary or secondary cells are administered. However, primary cells may be obtained for a donor (other than the recipient).

The term "primary cell" includes cells present in a suspension of cells isolated from a vertebrate tissue source (prior to their being plated i.e., attached to a tissue culture substrate such as a dish or flask), cells present in an explant derived from tissue, both of the previous types of cells plated for the first time, and cell suspensions derived from these plated cells. The term "secondary cell" or "cell strain" refers to cells at all subsequent steps in culturing. Secondary cells are cell strains which consist of secondary cells which have been passaged one or more times.

Primary or secondary cells of vertebrate, particularly mammalian, origin can be transfected with an exogenous nucleic acid sequence which includes a nucleic acid sequence encoding a signal peptide, and/or a heterologous nucleic acid sequence, e.g., encoding Foxn1, or an agonist or antagonist thereof, and produce the encoded product stably and reproducibly in vitro and in vivo, over extended periods of time. A heterologous amino acid can also be a regulatory sequence, e.g., a promoter, which causes expression, e.g., inducible expression or upregulation, of an endogenous sequence. An exogenous nucleic acid sequence can be introduced into a primary or secondary cell by homologous recombination as described, for example, in U.S. Pat. No.: 5,641,670. The transfected primary or secondary cells may also include DNA encoding a selectable marker which confers a selectable phenotype upon them, facilitating their identification and isolation.

Vertebrate tissue can be obtained by standard methods such a punch biopsy or other surgical methods of obtaining a tissue source of the primary cell type of interest. For example, punch biopsy is used to obtain skin as a source of fibroblasts or keratinocytes. A mixture of primary cells is obtained from the tissue, using known methods, such as enzymatic digestion or explanting. If enzymatic digestion is used, enzymes such as collagenase, hyaluronidase, dispase, pronase, trypsin, elastase and chymotrypsin can be used.

The resulting primary cell mixture can be transfected directly or it can be cultured first, removed from the culture plate and resuspended before transfection is carried out. Primary cells or secondary cells are combined with exogenous nucleic acid sequence to, e.g., stably integrate into their genomes, and treated in order to accomplish transfection. As used herein, the term "transfection" includes a variety of techniques for introducing an exogenous nucleic acid into a cell including calcium phosphate or calcium chloride precipitation, microinjection, DEAE-dextrin-mediated transfection, lipofection or electrophoration, all of which are routine in the art.

Transfected primary or secondary cells undergo sufficient number doubling to produce either a clonal cell strain or a heterogeneous cell strain of sufficient size to provide the therapeutic protein to an individual in effective amounts. The number of required cells in a transfected clonal heterogeneous cell strain is variable and depends on a variety of factors, including but not limited to, the use of the transfected cells, the functional level of the exogenous DNA in the transfected cells, the site of implantation of the transfected cells (for example, the number of cells that can be used is limited by the anatomical site of implantation), and the age, surface area, and clinical condition of the patient.

The transfected cells, e.g., cells produced as described herein, can be introduced into an individual to whom the product is to be delivered. Various routes of administration and various sites (e.g., renal sub capsular, subcutaneous, central nervous system (including intrathecal), intravascular, intrahepatic, intrasplanchnic, intraperitoneal (including intraomental), intramuscularly implantation) can be used.

One implanted in individual, the transfected cells produce the product encoded by the heterologous DNA or are affected by the heterologous DNA itself. For example, an individual who suffers from a pigmentation related disorder (e.g., vitiligo or albinism) is a candidate for implantation of cells producing an agent described herein, e.g., a Foxn1 polypeptide or a fragment or analog or mimic thereof as described herein.

An immunosuppressive agent e.g., drug, or antibody, can be administered to a subject at a dosage sufficient to achieve the desired therapeutic effect (e.g., inhibition of rejection of the cells). Dosage ranges for immunosuppressive drugs are known in the art. See, e.g., Freed et al. (1992) N. Engl. J. Med. 327:1549; Spencer et al. (1992) N. Engl. J. Med. 327:1541' Widner et al. (1992) n. Engl. J. Med. 327:1556). Dosage values may vary according to factors such as the disease state, age, sex, and weight of the individual.

Diagnostic Assays

The diagnostic assays described herein involve evaluating the Foxn1 signaling pathway in the subject, e.g., in a skin tissue. Various art-recognized methods are available for evaluating the activity of the Foxn1 signaling pathway or components thereof. For example, the method can include evaluating either the level of a Foxn1 pathway component (e.g., the level of Foxn1) and/or activity of the Foxn1 pathway. Techniques for detection of Foxn1 are known in the art and include, inter alia: antibody based assays such as enzyme immunoassays (EIA), radioimmunoassays (RIA), and Western blot analysis. Typically, the level in the subject is compared to the level and/or activity in a control, e.g., the level and/or activity in a tissue from a non-disease subject.

Techniques for evaluating binding activity, e.g., of Foxn1 to a Foxn1 binding partner, include fluid phase binding assays, affinity chromatography, size exclusion or gel filtration, ELISA, immunoprecipitation (e.g., the ability of an antibody specific to a first factor, e.g., Foxn1, to co-immunoprecipitate a second factor or complex, e.g., its receptor, with which the first factor can associate in nature).

Another method of evaluating the Foxn1 pathway in a subject is to determine the presence or absence of a lesion in or the misexpression of a gene which encodes a component of the Foxn1 pathway e.g., Foxn1. The method includes one or more of the following: detecting, in a tissue of the subject, the presence or absence of a mutation which affects the expression of a gene encoding Foxn1, or detecting the presence or absence of a mutation in a region which controls the expression of the gene, e.g., a mutation in the 5' control region; detecting, in a tissue of the subject, the presence or absence of a mutation which alters the structure of a gene encoding Foxn1; detecting, in a tissue of the subject, the misexpression of a gene encoding Foxn1, at the mRNA level, e.g., detecting a non-wild type level of a mRNA; and detecting, in a tissue of the subject, the misexpression of the gene, at the protein level, e.g., detecting a non-wild type level of a Foxn1 polypeptide.

In preferred embodiments the method includes: ascertaining the existence of at least one of: a deletion of one or more nucleotides from a gene encoding Foxn1; an insertion of one or more nucleotides into the gene, a point mutation, e.g., a substitution of one or more nucleotides of the gene, a gross chromosomal rearrangement of the gene, e.g., a translocation, inversion, or deletion.

For example, detecting the genetic lesion can include: (i) providing a probe/primer including an oligonucleotide containing a region of nucleotide sequence which hybridizes to a sense or antisense sequence from a Foxn1 gene, or naturally occurring mutants thereof or 5' or 3' flanking sequences naturally associated with the gene; (ii) exposing the probe/primer to nucleic acid of a tissue; and detecting, by hybridization, e.g., in situ hybridization, of the probe/primer to the nucleic acid, the presence or absence of the genetic lesion.

In preferred embodiments detecting the misexpression includes ascertaining the existence of at least one of: an alteration in the level of a messenger RNA transcript of a gene encoding Foxn1; the presence of a non-wild type splicing pattern of a messenger RNA transcript of the gene; or a non-wild type level of a gene encoding Foxn1.

In preferred embodiments the method includes determining the structure of a gene encoding Foxn1, an abnormal structure being indicative of risk for the disorder.

In preferred embodiments the method includes contacting a sample from the subject with an antibody to a component of the Foxn1 pathway, such as Foxn1, or a nucleic acid which hybridizes specifically with the gene.

Expression Monitoring and Profiling.

The presence, level, or absence of Foxn1 (protein or nucleic acid) in a biological sample can be evaluated by obtaining a biological sample from a test subject and contacting the biological sample with a compound or an agent capable of detecting the protein or nucleic acid (e.g., mRNA, genomic DNA) that encodes Foxn1 such that the presence of the protein or nucleic acid is detected in the biological sample. The term "biological sample" includes tissues, cells and biological fluids isolated from a subject, as well as tissues, cells and fluids present within a subject, e.g., urine. Preferred biological samples are serum or urine. The level of expression of Foxn1 can be measured in a number of ways, including, but not limited to: measuring the mRNA encoded by the Foxn1 gene; measuring the amount of protein encoded by Foxn1; or measuring the activity of the protein encoded by the gene.

The level of mRNA corresponding to Foxn1 in a cell can be determined both by in situ and by in vitro formats.

Isolated mRNA can be used in hybridization or amplification assays that include, but are not limited to, Southern or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length nucleic acid, or a portion thereof, such as an oligonucleotide of at least 7, 15, 30, 50, 100, 250 or 500 nucleotides in length and sufficient to specifically hybridize under stringent conditions to mRNA or genomic DNA of Foxn1. The probe can be disposed on an address of an array, e.g., an array described below. Other suitable probes for use in the diagnostic assays are described herein.

In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array described below. A skilled artisan can adapt known mRNA detection methods for use in detecting the level of mRNA encoded by the gene.

The level of mRNA in a sample that is encoded by a gene can be evaluated with nucleic acid amplification, e.g., by rtPCR (Mullis (1987) U.S. Pat. No. 4,683,202), ligase chain reaction (Barany (1991) Proc. Natl. Acad. Sci. USA 88:189-193), self sustained sequence replication (Guatelli et al., (1990) Proc. Natl. Acad. Sci. USA 87:1874-1878), transcriptional amplification system (Kwoh et al., (1989), Proc. Natl.

Acad. Sci. USA 86:1173-1177), Q-Beta Replicase (Lizardi et al., (1988) Bio/Technology 6:1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the gene being analyzed.

In another embodiment, the methods further contacting a control sample with a compound or agent capable of detecting mRNA, or genomic DNA, and comparing the presence of the mRNA or genomic DNA in the control sample with the presence of Foxn1 mRNA or genomic DNA in the test sample. In still another embodiment, serial analysis of gene expression, as described in U.S. Pat. No. 5,695,937, is used to detect transcript levels of Foxn1.

A variety of methods can be used to determine the level of Foxn1 protein. In general, these methods include contacting an agent that selectively binds to the protein, such as an antibody with a sample, to evaluate the level of protein in the sample. In a preferred embodiment, the antibody bears a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein.

The detection methods can be used to detect a component of the Foxn1 pathway, e.g., Foxn1, in a biological sample in vitro as well as in vivo. In vitro techniques for detection include enzyme linked immunosorbent assays (ELISAs), immunoprecipitations, immunofluorescence, enzyme immunoassay (EIA), radioimmunoassay (RIA), and Western blot analysis. In vivo techniques for detection of include introducing into a subject a labeled antibody. For example, the antibody can be labeled with a radioactive marker whose presence and location in a subject can be detected by standard imaging techniques. In another embodiment, the sample is labeled, e.g., biotinylated and then contacted to the antibody, e.g., an antibody positioned on an antibody array. The sample can be detected, e.g., with avidin coupled to a fluorescent label.

In another embodiment, the methods further include contacting the control sample with a compound or agent capable of detecting a Foxn1, and comparing the presence of Foxn1 protein in the control sample with the presence of the protein in the test sample.

The invention also includes kits for detecting the presence of Foxn1 in a biological sample. For example, the kit can include a compound or agent capable of detecting Foxn1 protein (e.g., an antibody) or mRNA (e.g., a nucleic acid probe); and a standard. The compound or agent can be packaged in a suitable container. The kit can further comprise instructions for using the kit to evaluate a subject, e.g., for risk or predisposition to a pigmentation related disorder.

The diagnostic methods described herein can identify subjects having, or at risk of developing, pigmentation-related disorders, such as vitiligo and melanoma. The prognostic assays described herein can be used to determine whether a subject can be administered an agent (e.g., Foxn1 or another agent described herein) to treat a pigmentation-related disorder.

Kits

An agent, e.g., a Foxn1 polypeptide, e.g., a Foxn1 polypeptide described herein, can be provided in a kit. The kit includes (a) Foxn1, e.g., a composition that includes Foxn1, and (b) informational material. The informational material can be descriptive, instructional, marketing or other material that relates to the methods described herein and/or the use of Foxn1 for the methods described herein. For example, the informational material relates to pigmentation.

In one embodiment, the informational material can include instructions to administer Foxn1 in a suitable manner to perform the methods described herein, e.g., in a suitable dose, dosage form, or mode of administration (e.g., a dose, dosage form, or mode of administration described herein). Preferred doses, dosage forms, or modes of administration are topical and percuatneous. In another embodiment, the informational material can include instructions to administer Foxn1 to a suitable subject, e.g., a human, e.g., a human having, or at risk for, a pigmentation related disorder.

The informational material of the kits is not limited in its form. In many cases, the informational material, e.g., instructions, is provided in printed matter, e.g., a printed text, drawing, and/or photograph, e.g., a label or printed sheet. However, the informational material can also be provided in other formats, such as Braille, computer readable material, video recording, or audio recording. In another embodiment, the informational material of the kit is contact information, e.g., a physical address, email address, website, or telephone number, where a user of the kit can obtain substantive information about Foxn1 and/or its use in the methods described herein. Of course, the informational material can also be provided in any combination of formats.

In addition to Foxn1, the composition of the kit can include other ingredients, such as a solvent or buffer, a stabilizer, a preservative, a fragrance or other cosmetic ingredient, and/or a second agent for treating a condition or disorder described herein, e.g., insulin or an obesity drug. Alternatively, the other ingredients can be included in the kit, but in different compositions or containers than Foxn1. In such embodiments, the kit can include instructions for admixing Foxn1 and the other ingredients, or for using Foxn1 together with the other ingredients.

Foxn1 can be provided in any form, e.g., liquid, dried or lyophilized form. It is preferred that Foxn1 be substantially pure and/or sterile. When Foxn1 is provided in a liquid solution, the liquid solution preferably is an aqueous solution, with a sterile aqueous solution being preferred. When Foxn1 is provided as a dried form, reconstitution generally is by the addition of a suitable solvent. The solvent, e.g., sterile water or buffer, can optionally be provided in the kit.

The kit can include one or more containers for the composition containing Foxn1. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of Foxn1. For example, the kit includes a plurality of syringes, ampules, foil packets, or blister packs, each containing a single unit dose of Foxn1. The containers of the kits can be air tight and/or waterproof.

The kit optionally includes a device suitable for administration of the composition, e.g., a syringe, inhalant, pipette, forceps, measured spoon, dropper (e.g., eye dropper), swab (e.g., a cotton swab or wooden swab), or any such delivery device. In a preferred embodiment, the device is a swab.

Generation of Variants: Production of Altered DNA and Peptide Sequences by Random Methods Amino acid sequence variants of Foxn1 polypeptides or fragments thereof can be prepared by a number of techniques, such as random mutagenesis of DNA which encodes a Foxn1 or a region thereof. Useful methods also include PCR mutagenesis and saturation mutagenesis. A library of random amino acid sequence variants can also be generated by the synthesis of a set of degenerate oligonucleotide sequences.

PCR Mutagenesis

In PCR mutagenesis, reduced Taq polymerase fidelity is used to introduce random mutations into a cloned fragment of DNA (Leung et al., 1989, *Technique* 1:11-15). This is a very powerful and relatively rapid method of introducing random mutations. The DNA region to be mutagenized is amplified using the polymerase chain reaction (PCR) under conditions that reduce the fidelity of DNA synthesis by Taq DNA polymerase, e.g., by using a dGTP/dATP ratio of five and adding $Mn^{2+}$ to the PCR reaction. The pool of amplified DNA fragments are inserted into appropriate cloning vectors to provide random mutant libraries.

Saturation Mutagenesis

Saturation mutagenesis allows for the rapid introduction of a large number of single base substitutions into cloned DNA fragments (Mayers et al., 1985, *Science* 229:242). This technique includes generation of mutations, e.g., by chemical treatment or irradiation of single-stranded DNA in vitro, and synthesis of a complimentary DNA strand. The mutation frequency can be modulated by modulating the severity of the treatment, and essentially all possible base substitutions can be obtained. Because this procedure does not involve a genetic selection for mutant fragments both neutral substitutions, as well as those that alter function, are obtained. The distribution of point mutations is not biased toward conserved sequence elements.

Degenerate Oligonucleotides

A library of homologs can also be generated from a set of degenerate oligonucleotide sequences. Chemical synthesis of a degenerate sequences can be carried out in an automatic DNA synthesizer, and the synthetic genes then ligated into an appropriate expression vector. The synthesis of degenerate oligonucleotides is known in the art (see for example, Narang, S A (1983) *Tetrahedron* 39:3; Itakura et al. (1981) *Recombinant DNA, Proc 3rd Cleveland Sympos. Macromolecules*, ed. A G Walton, Amsterdam: Elsevier pp 273-289; Itakura et al. (1984) *Annu. Rev. Biochem.* 53:323; Itakura et al. (1984) *Science* 198:1056; Ike et al. (1983) *Nucleic Acid Res.* 11:477. Such techniques have been employed in the directed evolution of other proteins (see, for example, Scott et al. (1990) *Science* 249:386-390; Roberts et al. (1992) *PNAS* 89:2429-2433; Devlin et al. (1990) *Science* 249: 404-406; Cwirla et al. (1990) *PNAS* 87: 6378-6382; as well as U.S. Pat. Nos. 5,223,409, 5,198,346, and 5,096,815).

Generation of Variants: Production of Altered DNA and Peptide Sequences by Directed Mutagenesis Non-random or directed mutagenesis techniques can be used to provide specific sequences or mutations in specific regions. These techniques can be used to create variants that include, e.g., deletions, insertions, or substitutions, of residues of the known amino acid sequence of a protein. The sites for mutation can be modified individually or in series, e.g., by (1) substituting first with conserved amino acids and then with more radical choices depending upon results achieved, (2) deleting the target residue, or (3) inserting residues of the same or a different class adjacent to the located site, or combinations of options 1-3.

Alanine Scanning Mutagenesis

Alanine scanning mutagenesis is a useful method for identification of certain residues or regions of the desired protein that are preferred locations or domains for mutagenesis, Cunningham and Wells (*Science* 244:1081-1085, 1989). In alanine scanning, a residue or group of target residues are identified (e.g., charged residues such as Arg, Asp, His, Lys, and Glu) and replaced by a neutral or negatively charged amino acid (most preferably alanine or polyalanine). Replacement of an amino acid can affect the interaction of the amino acids with the surrounding aqueous environment in or outside the cell. Those domains demonstrating functional sensitivity to the substitutions are then refined by introducing further or other variants at or for the sites of substitution. Thus, while the site for introducing an amino acid sequence variation is predetermined, the nature of the mutation per se need not be predetermined. For example, to optimize the performance of a mutation at a given site, alanine scanning or random mutagenesis may be conducted at the target codon or region and the expressed desired protein subunit variants are screened for the optimal combination of desired activity.

Oligonucleotide-Mediated Mutagenesis

Oligonucleotide-mediated mutagenesis is a useful method for preparing substitution, deletion, and insertion variants of DNA, see, e.g., Adelman et al., (*DNA* 2:183, 1983). Briefly, the desired DNA is altered by hybridizing an oligonucleotide encoding a mutation to a DNA template, where the template is the single-stranded form of a plasmid or bacteriophage containing the unaltered or native DNA sequence of the desired protein. After hybridization, a DNA polymerase is used to synthesize an entire second complementary strand of the template that will thus incorporate the oligonucleotide primer, and will code for the selected alteration in the desired protein DNA. Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al. (*Proc. Natl. Acad. Sci.* (1978) USA, 75: 5765).

Cassette Mutagenesis

Another method for preparing variants, cassette mutagenesis, is based on the technique described by Wells et al. (*Gene*, 34:315[1985]). The starting material is a plasmid (or other vector) which includes the protein subunit DNA to be mutated. The codon(s) in the protein subunit DNA to be mutated are identified. There must be a unique restriction endonuclease site on each side of the identified mutation site(s). If no such restriction sites exist, they may be generated using the above-described oligonucleotide-mediated mutagenesis method to introduce them at appropriate locations in the desired protein subunit DNA. After the restriction sites have been introduced into the plasmid, the plasmid is cut at these sites to linearize it. A double-stranded oligonucleotide encoding the sequence of the DNA between the restriction sites but containing the desired mutation(s) is synthesized using standard procedures. The two strands are synthesized separately and then hybridized together using standard techniques. This double-stranded oligonucleotide is referred to as the cassette. This cassette is designed to have 3' and 5' ends that are comparable with the ends of the linearized plasmid, such that it can be directly ligated to the plasmid. This plasmid now contains the mutated desired protein subunit DNA sequence.

Combinatorial Mutagenesis

Combinatorial mutagenesis can also be used to generate variants. For example, the amino acid sequences for a group of homologs or other related proteins are aligned, preferably to promote the highest homology possible. All of the amino acids which appear at a given position of the aligned sequences can be selected to create a degenerate set of combinatorial sequences. The variegated library of variants is generated by combinatorial mutagenesis at the nucleic acid level, and is encoded by a variegated gene library. For example, a mixture of synthetic oligonucleotides can be enzymatically ligated into gene sequences such that the degenerate set of potential sequences are expressible as individual peptides, or alternatively, as a set of larger fusion proteins containing the set of degenerate sequences.

Primary High-Through-Put Methods for Screening Libraries of Peptide Fragments or Homologs Various techniques are known in the art for screening peptides, e.g., synthetic peptides, e.g., small molecular weight peptides (e.g., linear or cyclic peptides) or generated mutant gene products. Techniques for screening large gene libraries often include cloning the gene library into replicable expression vectors, transforming appropriate cells with the resulting library of vectors, and expressing the genes under conditions in which detection of a desired activity, assembly into a trimeric molecules, binding to natural ligands, e.g., a receptor or substrates, facilitates relatively easy isolation of the vector encoding the gene whose product was detected. Each of the techniques described below is amenable to high through-put analysis for screening large numbers of sequences created, e.g., by random mutagenesis techniques.

Two Hybrid Systems

Two hybrid (interaction trap) assays can be used to identify a protein that interacts with Foxn1. These may include, e.g., agonists, superagonists, and antagonists of Foxn1. (The subject protein and a protein it interacts with are used as the bait protein and fish proteins.). These assays rely on detecting the reconstitution of a functional transcriptional activator mediated by protein-protein interactions with a bait protein. In particular, these assays make use of chimeric genes which express hybrid proteins. The first hybrid comprises a DNA-binding domain fused to the bait protein. e.g., Foxn1 or active fragments thereof. The second hybrid protein contains a transcriptional activation domain fused to a "fish" protein, e.g. an expression library. If the fish and bait proteins are able to interact, they bring into close proximity the DNA-binding and transcriptional activator domains. This proximity is sufficient to cause transcription of a reporter gene which is operably linked to a transcriptional regulatory site which is recognized by the DNA binding domain, and expression of the marker gene can be detected and used to score for the interaction of the bait protein with another protein.

Display Libraries

In one approach to screening assays, the candidate peptides are displayed on the surface of a cell or viral particle, and the ability of particular cells or viral particles to bind an appropriate receptor protein via the displayed product is detected in a "panning assay". For example, the gene library can be cloned into the gene for a surface membrane protein of a bacterial cell, and the resulting fusion protein detected by panning (Ladner et al., WO 88/06630; Fuchs et al. (1991) *Bio/Technology* 9:1370-1371; and Goward et al. (1992) *TIBS* 18:136-140). This technique was used in Sahu et al. (1996) J. Immunology 157:884-891, to isolate a complement inhibitor. In a similar fashion, a detectably labeled ligand can be used to score for potentially functional peptide homologs. Fluorescently labeled ligands, e.g., receptors, can be used to detect homolog which retain ligand-binding activity. The use of fluorescently labeled ligands, allows cells to be visually inspected and separated under a fluorescence microscope, or, where the morphology of the cell permits, to be separated by a fluorescence-activated cell sorter.

A gene library can be expressed as a fusion protein on the surface of a viral particle. For instance, in the filamentous phage system, foreign peptide sequences can be expressed on the surface of infectious phage, thereby conferring two significant benefits. First, since these phage can be applied to affinity matrices at concentrations well over $10^{13}$ phage per milliliter, a large number of phage can be screened at one time. Second, since each infectious phage displays a gene product on its surface, if a particular phage is recovered from an affinity matrix in low yield, the phage can be amplified by another round of infection. The group of almost identical *E. coli* filamentous phages M13, fd., and f1 are most often used in phage display libraries. Either of the phage gIII or gVIII coat proteins can be used to generate fusion proteins without disrupting the ultimate packaging of the viral particle. Foreign epitopes can be expressed at the $NH_2$-terminal end of pIII and phage bearing such epitopes recovered from a large excess of phage lacking this epitope (Ladner et al. PCT publication WO 90/02909; Garrard et al., PCT publication WO 92/09690; Marks et al. (1992) *J. Biol. Chem.* 267:16007-16010; Griffiths et al. (1993) *EMBO J* 12:725-734; Clackson et al. (1991) *Nature* 352:624-628; and Barbas et al. (1992) *PNAS* 89:4457-4461).

A common approach uses the maltose receptor of *E. coli* (the outer membrane protein, LamB) as a peptide fusion partner (Charbit et al. (1986) *EMBO* 5, 3029-3037). Oligonucleotides have been inserted into plasmids encoding the LamB gene to produce peptides fused into one of the extracellular loops of the protein. These peptides are available for binding to ligands, e.g., to antibodies, and can elicit an immune response when the cells are administered to animals. Other cell surface proteins, e.g., OmpA (Schorr et al. (1991) *Vaccines* 91, pp. 387-392), PhoE (Agterberg, et al. (1990) *Gene* 88, 37-45), and PAL (Fuchs et al. (1991) *Bio/Tech* 9, 1369-1372), as well as large bacterial surface structures have served as vehicles for peptide display. Peptides can be fused to pilin, a protein which polymerizes to form the pilus-a conduit for interbacterial exchange of genetic information (Thiry et al. (1989) *Appl. Environ. Microbiol.* 55, 984-993). Because of its role in interacting with other cells, the pilus provides a useful support for the presentation of peptides to the extracellular environment. Another large surface structure used for peptide display is the bacterial motive organ, the flagellum. Fusion of peptides to the subunit protein flagellin offers a dense array of may peptides copies on the host cells (Kuwajima et al. (1988) *Bio/Tech.* 6, 1080-1083). Surface proteins of other bacterial species have also served as peptide fusion partners. Examples include the *Staphylococcus* protein A and the outer membrane protease IgA of *Neisseria* (Hansson et al. (1992) *J. Bacteriol.* 174, 4239-4245 and Klauser et al. (1990) *EMBO J.* 9, 1991-1999).

In the filamentous phage systems and the LamB system described above, the physical link between the peptide and its encoding DNA occurs by the containment of the DNA within a particle (cell or phage) that carries the peptide on its surface. Capturing the peptide captures the particle and the DNA within. An alternative scheme uses the DNA-binding protein LacI to form a link between peptide and DNA (Cull et al. (1992) *PNAS USA* 89:1865-1869). This system uses a plasmid containing the LacI gene with an oligonucleotide cloning site at its 3'-end. Under the controlled induction by arabinose, a LacI-peptide fusion protein is produced. This fusion retains the natural ability of LacI to bind to a short DNA sequence known as LacO operator (LacO). By installing two copies of LacO on the expression plasmid, the LacI-peptide fusion binds tightly to the plasmid that encoded it. Because the plasmids in each cell contain only a single oligonucleotide sequence and each cell expresses only a single peptide sequence, the peptides become specifically and stably associated with the DNA sequence that directed its synthesis. The cells of the library are gently lysed and the peptide-DNA complexes are exposed to a matrix of immobilized receptor to recover the complexes containing active peptides. The associated plasmid DNA is then reintroduced into cells for amplification and DNA sequencing to determine the identity of the peptide ligands. As a demonstration of the practical utility of the method, a large random library of dodecapeptides was made and selected on a monoclonal antibody raised against the opioid peptide dynorphin B. A cohort of peptides was recovered, all related by a consensus sequence corresponding to a six-residue portion of dynorphin B. (Cull et al. (1992) *Proc. Natl. Acad. Sci. U.S.A.* 89-1869)

This scheme, sometimes referred to as peptides-on-plasmids, differs in two important ways from the phage display methods. First, the peptides are attached to the C-terminus of the fusion protein, resulting in the display of the library members as peptides having free carboxy termini. Both of the filamentous phage coat proteins, pIII and pVIII, are anchored to the phage through their C-termini, and the guest peptides are placed into the outward-extending N-terminal domains. In some designs, the phage-displayed peptides are presented right at the amino terminus of the fusion protein. (Cwirla, et al. (1990) *Proc. Natl. Acad. Sci. U.S.A.* 87, 6378-6382) A second difference is the set of biological biases affecting the population of peptides actually present in the libraries. The LacI fusion molecules are confined to the cytoplasm of the host cells. The phage coat fusions are exposed briefly to the cytoplasm during translation but are rapidly secreted through the inner membrane into the periplasmic compartment, remaining anchored in the membrane by their C-terminal hydrophobic domains, with the N-termini, containing the peptides, protruding into the periplasm while awaiting assembly into phage particles. The peptides in the LacI and phage libraries may differ significantly as a result of their exposure to different proteolytic activities. The phage coat proteins require transport across the inner membrane and signal peptidase processing as a prelude to incorporation into phage. Certain peptides exert a deleterious effect on these processes and are underrepresented in the libraries (Gallop et al. (1994) *J. Med. Chem.* 37(9):1233-1251). These particular biases are not a factor in the LacI display system.

The number of small peptides available in recombinant random libraries is enormous. Libraries of $10^7$-$10^9$ independent clones are routinely prepared. Libraries as large as $10^{11}$ recombinants have been created, but this size approaches the practical limit for clone libraries. This limitation in library size occurs at the step of transforming the DNA containing randomized segments into the host bacterial cells. To circumvent this limitation, an in vitro system based on the display of nascent peptides in polysome complexes has recently been developed. This display library method has the potential of producing libraries 3-6 orders of magnitude larger than the currently available phage/phagemid or plasmid libraries. Furthermore, the construction of the libraries, expression of the peptides, and screening, is done in an entirely cell-free format.

In one application of this method (Gallop et al. (1994) *J. Med. Chem.* 37(9):1233-1251), a molecular DNA library encoding $10^{12}$ decapeptides was constructed and the library expressed in an *E. coli* S30 in vitro coupled transcription/translation system. Conditions were chosen to stall the ribosomes on the mRNA, causing the accumulation of a substantial proportion of the RNA in polysomes and yielding complexes containing nascent peptides still linked to their encoding RNA. The polysomes are sufficiently robust to be affinity purified on immobilized receptors in much the same way as the more conventional recombinant peptide display libraries are screened. RNA from the bound complexes is recovered, converted to cDNA, and amplified by PCR to produce a template for the next round of synthesis and screening. The polysome display method can be coupled to the phage display system. Following several rounds of screening, cDNA from the enriched pool of polysomes was cloned into a phagemid vector. This vector serves as both a peptide expression vector, displaying peptides fused to the coat proteins, and as a DNA sequencing vector for peptide identification. By expressing the polysome-derived peptides on phage, one can either continue the affinity selection procedure in this format or assay the peptides on individual clones for binding activity in a phage ELISA, or for binding specificity in a completion phage ELISA (Barret, et al. (1992) *Anal. Biochem* 204,357-364). To identify the sequences of the active peptides one sequences the DNA produced by the phagemid host.

Secondary Screens

The high through-put assays described above can be followed (or substituted) by secondary screens in order to identify biological activities which will, e.g., allow one skilled in the art to differentiate agonists from antagonists. The type of a secondary screen used will depend on the desired activity that needs to be tested. For example, a pigmentation-related assay described herein can be used in which the ability to modulate, e.g., decrease or increase or mimic Foxn1 activity in skin can be used to identify Foxn1 agonists and antagonists from a group of peptide fragments isolated though one of the primary screens described above.

Peptide Mimetics

The invention also provides for production of the protein binding domains of Foxn1, to generate mimetics, e.g. peptide or non-peptide agents, e.g., agonists.

Non-hydrolyzable peptide analogs of critical residues can be generated using benzodiazepine (e.g., see Freidinger et al. in Peptides: Chemistry and Biology, G. R. Marshall ed., ESCOM Publisher: Leiden, Netherlands, 1988), azepine (e.g., see Huffman et al. in Peptides: Chemistry and Biology, G. R. Marshall ed., ESCOM Publisher: Leiden, Netherlands, 1988), substituted gama lactam rings (Garvey et al. in Peptides: Chemistry and Biology, G. R. Marshall ed., ESCOM Publisher: Leiden, Netherlands, 1988), keto-methylene pseudopeptides (Ewenson et al. (1986) J Med Chem 29:295; and Ewenson et al. in Peptides: Structure and Function (Proceedings of the 9th American Peptide Symposium) Pierce Chemical Co. Rockland, Ill., 1985), b-turn dipeptide cores (Nagai et al. (1985) Tetrahedron Lett 26:647; and Sato et al. (1986) J Chem Soc Perkin Trans 1:1231), and b-aminoalcohols (Gordon et al. (1985) Biochem Biophys Res Commun 126:419; and Dann et al. (1986) Biochem Biophys Res Commun 134:71).

EXAMPLES

Example

Foxn1 Expression

Foxn1 is expressed in melanocyte target cells of the hair follicle. Skin sections from wild-type mice (9 days old) were stained for Foxn1 by immunofluorescence; DNA was counterstained with Hoechst dye 33258 (blue). In the hair follicle, melanocytes form a cone-shaped cell cluster superficial to the follicular papilla (FP). This cell cluster transfers pigment to the epithelial precursor cells of the hair cortex (PC) and medulla, which differentiate as they move past the melanocytes towards the skin surface. Foxn1 is abundant in the differentiating cortical precursors. The protein localizes to cell nuclei, consistent with the function of a transcriptional activator. Thus, Foxn1 is normally associated with pigment recipients of the hair.

Example

Krt5-Foxn1 Transgenic Mice

To investigate Foxn1 function, we generated transgenic mice that, express Foxn1 from the keratin 5 promoter. Keratin 5 (or its binding partner keratin 14) is detected in the basal layer of the epidermis, the outer epithelial layer of the hair follicle (the infundibulum, isthmus, bulge region, and outer root sheath), and, in some studies, the matrix of the hair bulb, all of which contain cells capable of proliferation. In contrast, Foxn1 expression is associated with terminal differentiation and generally absent from epithelial cells with growth potential. Thus, the Krt5-Foxn1 transgene should misexpress Foxn1 in progenitor cell populations.

The Krt5-Foxn1 construct contains the complete coding sequence of the murine Foxn1 cDNA (nucleotides #97-2135). At the translation start site, a Flag epitope tag was fused to Foxn1's N-terminus, thus distinguishing exogenous Foxn1 from the endogenous protein. The Krt5promoter was provided by Dr. Mikhail Blumenberg (New York University) and shown to possess proper tissue-specific activity. From 5' to 3', the Krt5-Foxn1 transgene includes, from 5' to 3', the human Krt5 promoter (0.9 kb), the rabbit β-globin intron (0.75 kb), the murine Foxn1 cDNA (2.05 kb), and a human keratin 14 (Krt14) polyadenylation sequence (approximately 0.5 kb). The cDNA contains the complete Foxn1 coding sequence and has a Kozak sequence and Flag epitope tag added to the translation start site. The construct was injected into fertilized eggs of C57BL/6× DBA F1 hybrids at the CBRC Transgenic Core Facility (81). Transgenic animals were identified by PCR analysis of tail DNA, and lines were established by backcrossing to strain C57BL/6.

To examine the transgene's morphological effects, skin sections were stained with hematoxylin and eosin. Transgenic epidermis often displayed small dark granules in the basal layer, while such granules were not found in wild-type epidermis. Since the granules resembled melanin, skin sections were stained using the Masson-Fontana technique, which produces a black stain specific to melanin. The transgenic epidermis showed strong Masson-Fontana staining, primarily in the basal layer but also occasionally in suprabasal layers. Within the basal layer, much, if not most, of the staining was located in keratinocytes. In contrast to transgenic skin, no staining was observed in wild-type epidermis. Thus, the Krt5-Foxn1 transgene induced the accumulation of melanin in epidermal cells. In regions of the body with little or no hair, for example, the faces and paws of a 3-week-old transgenic mouse, the transgene causes a visible darkening of the skin.

The transgene also affected the pigmentation of sites neighboring the epidermis, as Masson-Fontana staining was observed in the infundibulum and sebaceous gland; such staining was absent in wild-type skin. In other parts of the hair follicle, the transgenic and wild-type animals exhibited similar Masson-Fontana staining patterns, as melanin was abundant in the hair shaft and bulb. At the macroscopic level, the transgenic coat appeared normal in color and density, suggesting that the transgene did not decrease the total number of follicular melanocytes. Thus, the epidermal pigmentation did not result from a general impairment of melanocyte migration, as melanocytes entered the hair bulbs and provided pigment to the hair.

To assess pigment cell status, skin sections were stained by TTA (tyramide-based tyrosinase assay), a histochemical technique to identify the sites of active tyrosinase, an enzyme essential for melanin synthesis and one of the best markers of pigment cells. In accord with the Masson-Fontana staining, transgenic epidermis displayed a far greater number of TTA-positive cells than wild-type epidermis. These transgenic cells were located principally in the basal layer, though some suprabasal cells were also stained by TTA. In shape, the TTA-positive cells often possessed a flattened, extended appearance, resembling dendritic pigment cells rather than keratinocytes. Near follicular orifices, TTA stained basal cells of the transgenic infundibulum and sebaceous gland, again matching the distribution of melanin. In parallel with these assays, skin sections were stained for Kit, a receptor tyrosine kinase present on melanocytes, mast cells, germ cells, and hematopoietic stem cells. The Kit staining pattern was identical to that of TTA, as Kit-positive cells were observed throughout the basal layers of transgenic epidermis, infundibulum, and sebaceous glands; few, if any, such cells were found in the corresponding regions of wild-type skin. Thus, transgenic skin possessed numerous melanocytes in the epidermis and superficial portions of the hair follicle. Consistent with the distribution of melanocytes, the Flag-tagged Foxn1 was detected by immunofluorescence in epidermal keratinocytes, infundibular epithelial cells, and sebocyte precursors, all of which were located in the basal layer.

The Krt5-Foxn1 transgene altered the development of the skin's pigmentary system. Whereas the epidermis normally loses melanocyte precursors after birth, Foxn1 misexpression caused the epidermis (and neighboring follicular regions) to retain some of these cells and acquire pigment. Despite this retention of pigment cells, other melanocyte precursors followed their normal route into the hair follicles, formed a cone-shaped cluster in the hair bulb, and transferred pigment to the hair. Thus, the transgene reshaped the pigmentary system, inducing a more human-like organization, as melanocytes targeted both the epidermis and hair for melanization.

Epidermal melanocytes were observed in three different lines of Krt5-Foxn1 transgenics. Since the lines were derived from different founders, the phenotype must result from the transgene itself rather than the site of insertion.

In wild-type murine skin, epithelial cells express endogenous Foxn1 during the early stages of terminal differentiation. At birth, Foxn1 is expressed in many epidermal cells, as the newborn epidermis is relatively thick and contains many differentiating cells. Shortly after birth however, the epidermis exhibits a decline in self-renewal activity, as fewer cells either proliferate or differentiate. Consequently, the epidermis thins, eventually decreasing to almost a single living layer. Concomitant with this thinning, Foxn1 expression becomes sporadic or rare. Perhaps significantly, this thinning period is also the time at which the melanoblasts disappear from the epidermis. Thus, as the epidermis matures, there is a simultaneous decline in Foxn1 expression, melanoblast numbers, and self-renewal activity.

In the hair follicles, Foxn1 expression is associated primarily with anagen, when differentiating cells are produced at the highest rate. During anagen, Foxn1 is most abundant in the differentiating precursors of the cortex, the structure most affected by nude mutations. In addition, Foxn1 is detected in the precursors of the medulla, though at lower levels. In the hair bulb, the pre-cortical and -medullary cells are the only cell types that form productive contacts with melanocytes and receive pigment. Thus, as the hair acquires melanin, Foxn1 is present in melanocyte target cells. Moreover, given the strong expression and effects of Foxn1 in the cortex, Foxn1 activity appears greatest in melanocyte target cells. Taking all results together, we propose that Foxn1 promotes the functional association of melanocytes and epithelial cells, perhaps inducing the development of epithelial-melanin units. To perform this function, Foxn1 presumably causes epithelial cells to emit signals, which in turn stimulate melanocytes to provide pigment to the Foxn1-positive cells. By such a mechanism, an epithelial cell could induce and control its own pigmentation.

FGF2 was strongly induced in patches of Krt5-Foxn1 epidermis. Within these patches, Fgf2 was located primarily in the basal layer, and much of this protein seemed associated with the basement membrane (an established site of Fgf2 localization). It is known that Fgf2 has "pro-pigmentary" effects, as this factor is a potent melanocyte mitogen, and a potential inducer of melanocyte differentiation and migration. Moreover, Fgf2 stimulates the multiplication of several epithelial cell types, including epidermal keratinocytes and ductal cells of the mammary gland. Thus, based on its known properties, FGF2 is a good effector candidate, and its induction can explain, at least in part, how Foxn1 promotes epithelial pigmentation and self-renewal.

Compared to wild-type skin, transgenic skin possesses high levels of Fgf2 in the epidermis. Much of this protein is located in the basal layer, the site of transgene expression. To measure Fgf2 quantitatively, epithelial cells were isolated from murine skin and grown in culture; the medium conditioned by these cultures was then collected and assayed for Fgf2 by ELISA. Under these in vitro conditions, transgenic epithelial cells secrete approximately 6-fold more Fgf2 than wild-type (WT) cells. For a quantitative comparison of Fgf2 mRNA levels, epithelial cells were isolated from the skin of wild-type mice, grown in culture, and infected with recombinant adenoviruses. These recombinant adenoviruses, designated Ad and Ad-Foxn1, were derived from the ADEASY™ vector system. Ad-Foxn1 expresses the same Flag-tagged Foxn1 cDNA as the transgene, while Ad is the empty vector, to serve as a control. At 24 hours post-infection, Fgf2 mRNA was measured by real-time RT-PCR. Similar to the Krt5-Foxn1 transgene, the Ad-Foxn1 virus strongly stimulates Fgf2 expression, as Ad-Foxn1-infected cultures possess 13-fold more Fgf2 mRNA than Ad-infected cultures.

Foxn1 binds to sites within or near the chromosomal Fgf2 gene. Wild-type epithelial cells were isolated from murine skin, grown in culture, and infected with Ad or Ad-Foxn1. The binding of Foxn1 to chromosomal DNA was then assayed by chromatin immunoprecipitation (ChIP). In these assays, protein-DNA complexes were precipitated with antibodies to Flag and quantitated by real-time PCR. The ChIP assays identified two sites that bind Foxn1 and lie in cis with Fgf2. Site 1 is located upstream from the Fgf2 core promoter, e.g., within 700, 500, 300, or 200 base pairs of the core promoter. Site 2 is located in the first intron of Fgf2. Since this intronic region is conserved, it may provide a critical regulatory function.

As seen, Foxn1 binds to cis elements of Fgf2, stimulates Fgf2 transcript levels, and induces the secretion of Fgf2 protein. The results suggest that Foxn1 is a direct activator of Fgf2 and that Fgf2 is a downstream effector of Foxn1. Given its effects on melanocyte behavior, Fgf2 is a likely mediator of Foxn1's influence on pigmentary system development.

In wild-type mice, the epidermis acquires little if any melanin, as melanocytes are confined primarily to the hair follicles and (to a lesser extent) dermis. In contrast, transgenic mice display high levels of melanin in the epidermis and neighboring regions of the hair follicle, such as the infundibulum (IF) and sebaceous gland (SG). No differences are observed in the melanization of the hair shafts (HS), as transgenic hairs are as richly pigmented as wild-type hairs. Thus, the transgene converts the epidermis into a pigmented tissue without adversely affecting the pigmentation of the hair coat. Skin sections from 6-day-old mice were stained for tyrosinase activity using Tyramide-based Tyrosinase Assay, a technique that specifically detects melanocytes; DNA was counterstained with Hoechst dye 33258. After birth, wild-type skin rapidly loses melanocytes from the epidermis. In contrast, transgenic skin retains numerous melanocytes in the epidermis as well as superficial portions of the hair follicle.

Skin sections from 9-day-old mice were stained for Foxn1 and DNA. In wild-type skin, Foxn1 is induced as epidermal cells lose the ability to divide and initiate terminal differentiation; shortly after birth, these Foxn1-positive cells become rare, as the epidermis thins and few cells divide or differentiate. Transgenic skin, as expected, exhibits a much larger population of Foxn1-positive epithelial cells; like the melanocytes, these transgene-expressing cells are detected in the basal layer of the epidermis, infundibulum, and sebaceous gland. Thus, in transgenic skin, melanocytes localize to sites of transgene activity. The transgene broadens the actions of the pigmentary system. By misexpressing Foxn1, the epidermis joins the hair as a target for pigmentation, and the melanocyte population reorganizes to match its expanded target.

Foxn1 is essential for proper pigmentation of the hair shaft. Skin was biopsied from 1-month-old mice that were heterozygous (Foxn1 +/−; upper panel) or homozygous (Foxn1 −/−; lower panel) for a null mutation in Foxn1. The null mutation is recessive, and thus the heterozygous mice were phenotypically normal. The skin samples were sectioned and stained for melanin using the Masson-Fontana technique. Whereas Foxn1 +/− hair shafts develop a cortex that is richly and uniformly pigmented, Foxn1 −/− hair shafts display severe hypopigmentation of the cortex, as melanin granules are sparse and unevenly distributed among cortical cells. While failing to pigment the cortex, the melanocytes themselves were capable of normal development and melanin transfer, as the medulla is well-pigmented in Foxn1 −/− hair shafts. Given the strong expression of Foxn1 in wild-type cortical epithelium, the hypopigmentation must result from a defect in the cortical epithelial cells. Thus, a loss of Foxn1 function impairs epithelial melanization, while a gain of Foxn1 function (the Krt5-Foxn1 transgene) induces a novel melanization. These results demonstrate that Foxn1 normally promotes the acquisition of pigment by epithelial cells and that it does so (at least in part) by enabling epithelial cells to control the behavior of melanocytes.

Without intending to be bound by theory, Foxn1 may function in the development of the skin by a variety of mechanisms. In the epidermis and hair follicles, epithelial cells induce Foxn1 as they lose the ability to multiply and initiate terminal differentiation. As Foxn1 accumulates, it activates the downstream effectors of its pathway, which in turn promote up to three developmental processes. The first process is epithelial differentiation. Within a Foxn1-expressing cell, Foxn1 stimulates early features of terminal differentiation and suppresses later features, enabling the cell to proceed through its differentiation program in proper sequence. The second process is epithelial growth or self-renewal. As a cell begins its differentiation program, Foxn1 induces the cell to release growth factors, and these growth factors then stimulate neighboring epithelial cells (which lack Foxn1) to divide. In this way, the differentiating cell is replaced as it leaves the pool of proliferating cells, and the progenitor population maintains a constant size. The third process is epithelial melanization. That is, Foxn1 promotes the functional association of epithelial cells and melanocytes, identifying an epithelial cell as a target for pigmentation and inducing the intercellular contacts required for pigment transfer. To perform this pigmentary function, Foxn1 causes epithelial cells to emit signals, which in turn stimulate melanocytes to melanize the Foxn1-expressing epithelium. Thus, according to this model, Foxn1 plays a unique role in the development of cutaneous epithelia, as the protein provides a link or nexus connecting differentiation, proliferation, and pigmentation. Foxn1 accomplishes part of its function via Fgf2, a known positive regulator of epithelial cell division and melanocyte activity. Other effectors most likely exist as well, and these factors should cooperate with Fgf2 in the transmission of Foxn1's instructions to the skin.

A number of embodiments of the invention have been described. Nevertheless, it will be understood that various modifications may be made without departing from the spirit and scope of the invention. Accordingly, other embodiments are within the scope of the following claims. Unless otherwise defined, all technical and scientific terms used herein have the same meaning as commonly understood by those of ordinary skill in the art to which this invention belongs. All publications, patent applications (including U.S. Ser. No. 60/525,093, filed Nov. 26, 2004), patents, and other references mentioned herein are incorporated by reference in their entirety. In case of a conflict in terminology, the present specification will control. In addition, the described materials and methods are illustrative only and are not intended to be limiting.

We claim:

1. A method of identifying an agent that modulates skin pigmentation, said method comprising:
    evaluating a test agent for the ability to modulate Foxn1 expression or Foxn1 activity or level; and
    identifying the test agent as an agent that modulates skin pigmentation if the test agent modulates Foxn1 expression or Foxn1 activity or level.

2. The method of claim 1, wherein the test agent is evaluated on a cell.

3. The method of claim 2, wherein the genome of the cell comprises a transgene encoding a reporter molecule operably linked to a Foxn1 promoter.

4. The method of claim 1, further comprising:
    contacting a test agent with a cultured cell; and
    monitoring the cell for a change in pigmentation, wherein altered pigmentation is indicative of the effect of the test agent on pigmentation.

5. The method of claim 4, wherein the cell is a pigmented cell type.

6. The method of claim 4, wherein the cell comprises a Foxn1 transgene.

7. The method of claim 1, further comprising:
    contacting a culture comprising a melanocyte and a non-melanocyte cell with a test agent; and monitoring the culture for a change in pigmentation, wherein altered pigmentation is indicative of the effect of the test agent on pigmentation.

8. The method of claim 2, wherein the cell is a cultured cell.

9. The method of claim 8, wherein the cell is within an explant.

10. The method of claim 2, wherein the test agent is a composition that contains a chemical compound at at least 10% purity.

* * * * *

UNITED STATES PATENT AND TRADEMARK OFFICE
CERTIFICATE OF CORRECTION

| | | |
|---|---|---|
| PATENT NO. | : 7,687,265 B2 | Page 1 of 1 |
| APPLICATION NO. | : 10/997202 | |
| DATED | : March 30, 2010 | |
| INVENTOR(S) | : Brissette et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 354 days.

Signed and Sealed this
Twenty-second Day of February, 2011

David J. Kappos
*Director of the United States Patent and Trademark Office*